(12) United States Patent
Miller et al.

(10) Patent No.: US 7,241,774 B2
(45) Date of Patent: Jul. 10, 2007

(54) SUBSTITUTED TETRAHYDROISOQUINOLINE COMPOUNDS, METHODS OF MAKING, AND THEIR USE

(75) Inventors: Duane D. Miller, Germantown, TN (US); Eldon E. Geisert, Jr., Germantown, TN (US); Michael Mohler, Cordova, TN (US); Victor Nikulin, Memphis, TN (US); Oleg Kirichenko, Memphis, TN (US); Seoung Sung Hong, Collierville, TN (US); Gyong Suk Kang, Pusan (KR); Igor Rakov, Memphis, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 10/389,651

(22) Filed: Mar. 13, 2003

(65) Prior Publication Data

US 2004/0019078 A1    Jan. 29, 2004

Related U.S. Application Data

(60) Provisional application No. 60/363,952, filed on Mar. 13, 2002.

(51) Int. Cl.
*C07D 217/02* (2006.01)
*A61K 31/47* (2006.01)
(52) U.S. Cl. ..................... 514/307; 546/139
(58) Field of Classification Search ............... 514/307; 546/139
See application file for complete search history.

(56) References Cited

U.S. PATENT DOCUMENTS

| 5,919,639 A | 7/1999 | Humphreys et al. |
| 5,919,795 A | 7/1999 | Chang et al. |
| 6,025,355 A | 2/2000 | Reddy et al. |
| 6,043,253 A | 3/2000 | Brockunier et al. |
| 6,117,898 A | 9/2000 | MacDonald et al. |
| 6,121,283 A | 9/2000 | Chang et al. |
| 6,194,428 B1 | 2/2001 | Urbahns et al. |

FOREIGN PATENT DOCUMENTS

| JP | 01143833 | 6/1989 |
| WO | WO 90/02119 | 3/1990 |
| WO | WO 00/53572 | 9/2000 |
| WO | WO 01/55117 | 8/2001 |

OTHER PUBLICATIONS

Parmee et al, Bioorganic & Medicinal Chemistry, vol. 10, pp. 2283-2286, Jun. 2000.*
Markovich et al, Journal of Medicinal Chemistry, vol. 35, pp. 466-479, 1992.*
Bermejo et al., "Syntheses and Antitumor Targeting G1 Phase of the Cell Cycle of Benzoyldihydroisoquinolines and Related 1-Substituted Isoquinolines," *J. Med. Chem.* 45:5058-5068 (2002).

* cited by examiner

*Primary Examiner*—Zinna N. Davis

(57) ABSTRACT

The present invention relates to novel substituted tetrahydroisoquinoline compounds, pharmaceutical compositions containing the compounds, methods of making the compounds, and methods of using the compounds to destroy a target cell, such as a cancer cell, and to treat or prevent a cancerous condition.

7 Claims, 8 Drawing Sheets

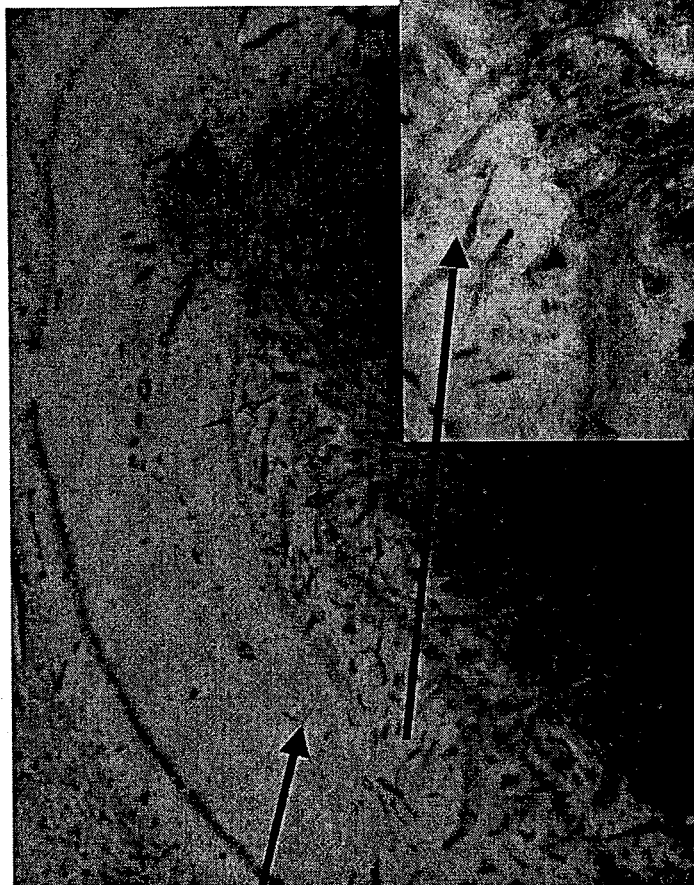
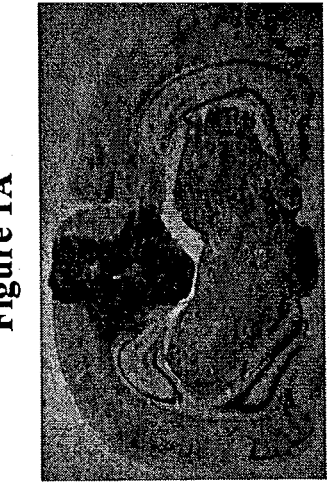
Figure 1E
Figure 1D
Figure 1A
Figure 1B
Figure 1C

SUBSTITUTED TETRAHYDROISOQUINOLINE COMPOUNDS, METHODS OF MAKING, AND THEIR USE

This application claims the benefit of U.S. Provisional Patent Application Ser. No. 60/363,952, filed Mar. 13, 2002, which is hereby incorporated by reference in its entirety.

FIELD OF THE INVENTION

The present invention relates generally to the production and use of substituted tetrahydroisoquinoline compounds.

BACKGROUND OF THE INVENTION

Despite decades of research, the prognosis of most of the 17,500 patients diagnosed annually with brain cancer is very poor. The mortality rate of brain cancer patients is about 80 percent, second only to lung cancer patients whose moratality rate is about 85 percent (Bethune et al., *Pharm. Res.* 16(6):896-905 (1999)). The standard treatment is surgical excision and radiation therapy with or without adjuvant chemotherapy. Unfortunately, the Food and Drug Administration has not approved many new drugs for treatment of brain cancer over the last three decades. As of 1997, carmustine ("BCNU"), lomustine ("CCNU"), procarbazine, and vincristine were still the most commonly used drugs for both newly diagnosed and recurrent gliomas (Prados et al., *Sem. Surgical Oncol.* 14:88-95 (1998)). The use of adjuvant chemotherapy is currently controversial because very few patients respond to the standard chemotherapeutic protocols (Mason et al., *J. Clin. Oncol.* 15(12):3423-3427 (1997), although assay have been developed to identify which patients are likely to respond to chemotherapies. While these assays have improved survival rates slightly, the responsive tumors are in the minority and mortality rates remain high.

Numerous experimental trials have been attempted over the years with limited success. The most successful protocols (i.e., those that progressed to phase II clinical trials) involved combination therapies. The majority of single therapies did not pass phase I trials. Molecules such as the prototypical isoquinoline PX1195, benzodiazepine $R_0$5-4864, and the recently reported pyrrolobenzoxazepine NF 182 (Zisterer et al., *Biochem. Pharmacol.* 55:397-403 (1998)) form a class of agents that bind to the peripheral benzodiazepine receptors ("PBR") and possess antiproliferative activity toward C6 glioma cells. The $EC_{50}$ values for these agents are 73 µM, 95 µM, and 37.5 µM, respectively. While these PBR ligands have been useful as brain cancer imaging agents (Olsen et al., *Cancer Res.* 48:5837-5841 (1988)), they have not been demonstrated to be useful for treating cancer. Thus, a need exists to identify compounds having improved antiproliferative/cytotoxic activity on brain and/or other forms of cancer.

The present invention is directed to overcoming these and other deficiencies in the art.

SUMMARY OF THE INVENTION

A first aspect of the present invention relates to a compound according to formula (I) as follows:

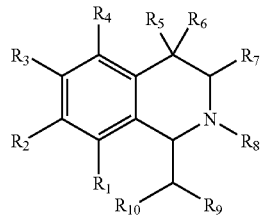

wherein, $R_1$, $R_2$, $R_3$, and $R_4$ are independently hydrogen, hydroxyl, halide, alkyl, aryl, alkoxy, aryloxy, amino, alkylamino, or dialkylamino;

$R_5$ and $R_6$ are independently hydrogen, alkyl, or aryl;

$R_7$ is hydrogen, alkyl, alkylester, arylester, alkylamido, dialkylamido, arylamido, or $R_6$ and $R_7$ together are —$(CH_2)_k$— forming a ring structure fused with the N-hetero ring of (I), where k is either 3 or 4;

$R_8$ is hydrogen, alkyl, arylalkyl, or aryl;

$R_9$ is

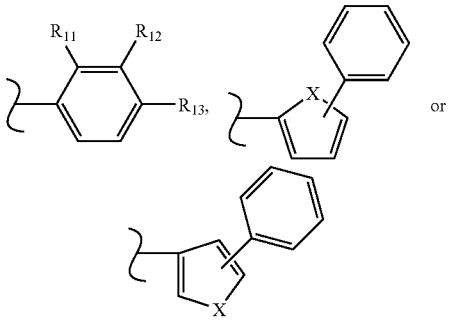

where X is oxygen, sulfur or nitrogen,

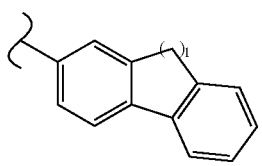

where l is 1 or 2,

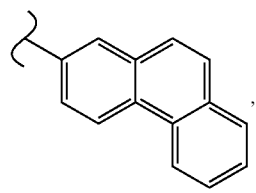

or $R_8$ and $R_9$ together are

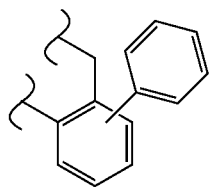

forming a ring structure fused with the N-hetero ring of (I);

R$_{10}$ is hydrogen or R$_1$ and R$_{10}$ together are —(CH$_2$)$_2$— forming a ring structure fused with both the benzene ring and the N-hetero ring of (I);

R$_{11}$, R$_{12}$, and R$_{13}$ are independently hydrogen, hydroxyl, halide, alkyl, arylalkyl, alkenyl, arylalkenyl, alkoxy, aryloxy, amino, alkylamino, dialkylamino, arylamino, aryl, cyclohexyl, or

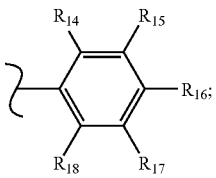

and

R$_{14}$, R$_{15}$, R$_{16}$, R$_{17}$, and R$_{18}$ are independently hydrogen, hydroxyl, halide, alkyl, alkoxy, amino, alkylamino, or dialkylamino.

A second aspect of the present invention relates to a compound according to formula (II) as follows:

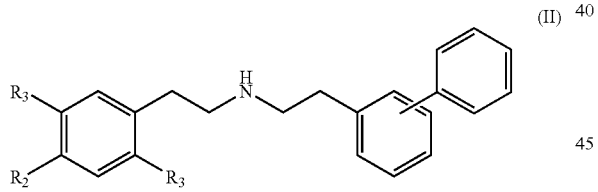

(II)

wherein R$_1$, R$_2$, and R$_3$ are independently hydrogen, hydroxyl, halide, alkyl, aryl, alkoxy, aryloxy, amino, alkylamino, or dialkylamino.

A third aspect of the present invention relates to a pharmaceutical composition that includes a pharmaceutically acceptable carrier and a compound of the present invention.

A fourth aspect of the present invention relates to a method of destroying a target cell that includes: providing a compound of the present invention and contacting a target cell with the compound under conditions effective to destroy the target cell.

A fifth aspect of the present invention relates to a method of treating or preventing a cancerous condition that includes: providing a compound of the present invention and administering an effective amount of the compound to a patient under conditions to treat an existing cancerous condition or prevent development of a cancerous condition.

A sixth aspect of the present invention relates to a method of preparing a tetrahydroisoquinoline compound of the present invention wherein R$_9$ is

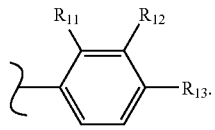

This method is carried out by reacting a precursor of formula

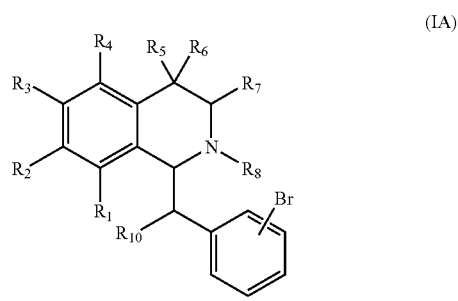

(IA)

with Q—B(OH)$_2$ under conditions effective to replace the bromo group with —Q at the ortho, meta, or para position, wherein Q is alkyl, arylalkyl, alkenyl, arylalkenyl, alkoxy, aryloxy, aryl, cyclohexyl, or

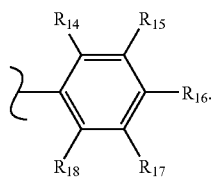

A seventh aspect of the present invention relates to another method of preparing a tetrahydroisoquinoline compound of the present invention. This method is carried out by treating a precursor of formula (IB)

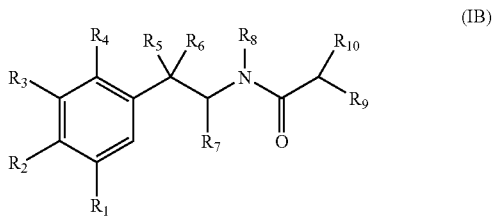

(IB)

under conditions effective to form a six-membered N-hetero ring fused with the phenyl, thereby forming the compound of formula (I).

An eighth aspect of the present invention relates to a method of preparing a compound according to formula (II) of the present invention. This method is carried out by treating a compound having the structure

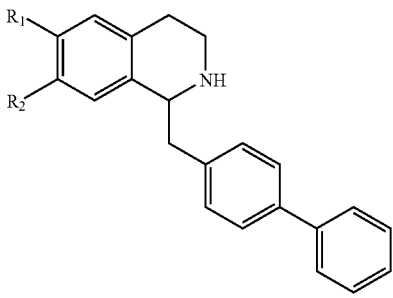

under conditions effective to open the N-hetero ring between C-1 and the phenyl ring, thereby forming the compound according to formula (II).

The compounds of the present invention have been demonstrated to be effective, both in vitro and in vivo, in destroying cancer cells and thus for the treatment of various forms of cancer including, without limitation, brain cancer, lung cancer, breast cancer, prostate cancer, cervical cancer. Several compounds of the present invention have shown greater efficacy than conventional therapeutics in destroying cancer cells and, significantly, causes less harm to normal cells. Without being bound by theory, it is believed that the compounds of the present invention are capable of destroying mitochondria and thereby disrupt cellular metabolism in cancer cells, eventually leading to ablation of the treated cells. As a result of their efficacy, the compounds of the present invention can afford effective treatments for various forms of cancer, such as glioma or glioblastoma brain cancers, which historically have low long-term survival rates.

BRIEF DESCRIPTION OF THE DRAWINGS

FIGS. 1A-E illustrate the growth of C6 glioma in the brains of rats with vehicle only as control (1A-C), the anti-cancer drug BCNU (1D), and 6,7-bis-hydroxy-1-biphenyl-4-ylmethyl-1,2,3,4-tetrahydro-isoquinoline hydrochloride (designated MMGS-155) (1E). Approximately $5 \times 10^4$ C6 glioma cells were transplanted into a rat brain via a cannula and then the rat was immediately treated for seven days. Tumor cells are depicted by staining for beta galactosidase. Regions of the control treatment are shown at higher magnifications (1B and 1C) to illustrate the invasiveness of the glioma tumor. At the highest magnification (1C), the infiltration of the tumor along blood vessels can be observed.

In FIG. 9A, C6 glioma cells were treated with MMGS-155 (■) and BCNU (•) for 96 hr. 6,7-bis-hydroxy-1-biphenyl-4-ylmethyl-1,2,3,4-tetrahydro-isoquinoline hydrochloride showed greater anti-proliferative activity than BCNU. In FIG. 9B, the selectivity of BCNU and 6,7-bis-hydroxy-1-biphenyl-4-ylmethyl-1,2,3,4-tetrahydro-isoquinoline hydrochloride on C6 glioma cells relative to primary cultured cortical astrocytes is shown for concentrations at $EC_{50}$.

DETAILED DESCRIPTION OF THE INVENTION

Figure 2:
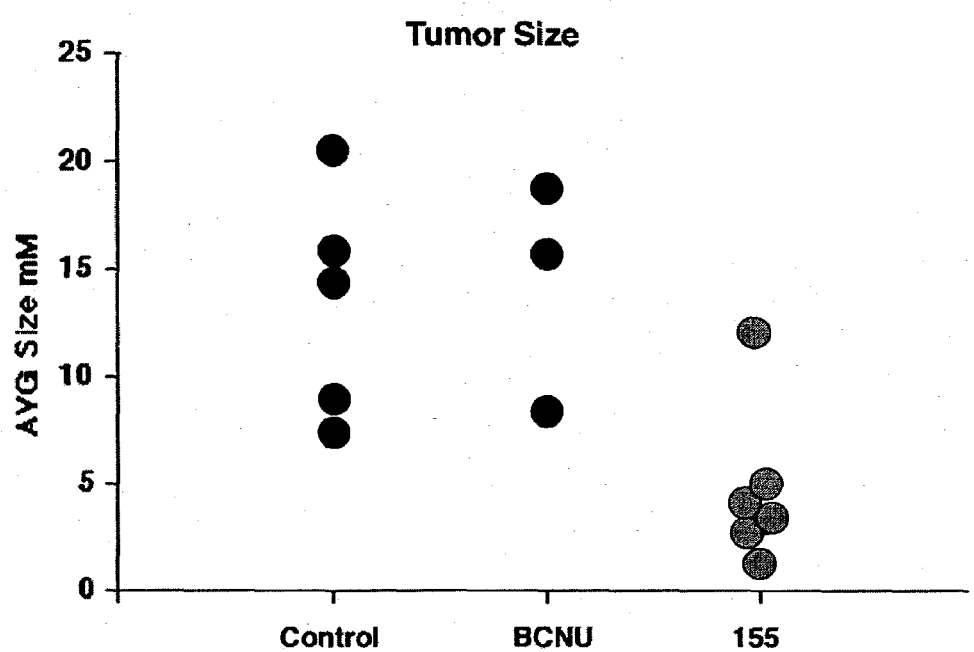
FIG. 2 is a graph depicting the maximum extent of tumor in a single section. The control, BCNU, and 6,7-bis-hydroxy-1-biphenyl-4-ylmethyl-1,2,3,4-tetrahydro-isoquinoline hydrochloride (MMGS-155) treatments are described as in FIG. 1. There was no significant size (area) difference in the control and BCNU-treated rats. The rats treated with MMGS-155 had tumors significantly smaller than the control groups (Mann-Whitney U test, p=0.009).

The present invention relates generally to substituted tetrahydro-isoquinoline compounds, compositions that contain such compounds, methods for preparing such compounds, and their use for ablating cancer cells.

The compounds of the present invention include compounds of formulae (I) and (II) as set forth below.

The compounds of formula (I) include:

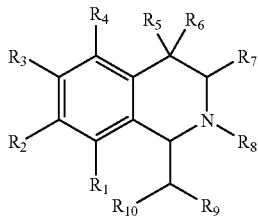
(I)

wherein, $R_1$, $R_2$, $R_3$, and $R_4$ are independently hydrogen, hydroxyl, halide, alkyl, aryl, alkoxy, aryloxy, amino, alkylamino, or dialkylamino;

$R_5$ and $R_6$ are independently hydrogen, alkyl, or aryl;

$R_7$ is hydrogen, alkyl, alkylester, arylester, alkylamido, dialkylamido, arylamido, or $R_6$ and $R_7$ together are —$(CH_2)_k$— forming a ring structure fused with the N-hetero ring of (I), where k is ei $R_8$ is hydrogen, alkyl, aryl, or arylalkyl;

$R_9$ is

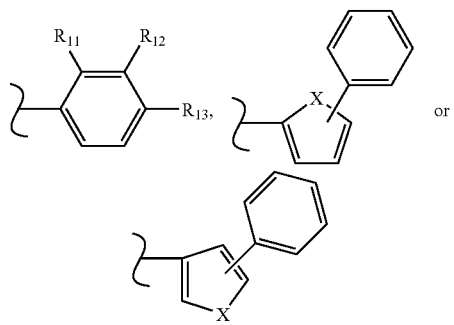
or where X is oxygen, sulfur, or nitrogen,

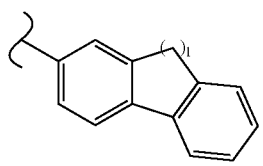

where l is 1 or 2,

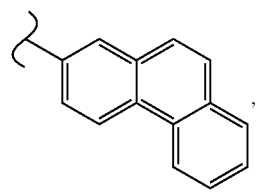, or $R_8$ and $R_9$ together are

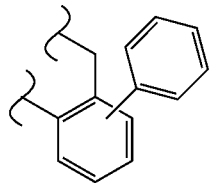

forming a ring structure fused with the N-hetero ring of (I);

$R_{10}$ is hydrogen or $R_1$ and $R_{10}$ together are —$(CH_2)_2$— forming a ring structure fused with both the benzene ring and the N-hetero ring of (I);

$R_{11}$, $R_{12}$, and $R_{13}$ are independently hydrogen, hydroxyl, halide, alkyl, arylalkyl, alkenyl, alkoxy, aryloxy, amino, alkylamino, dialkylamino, arylamino, aryl, cyclohexyl, or

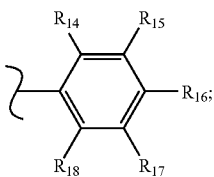

and $R_{14}$, $R_{15}$, $R_{16}$, $R_{17}$, and $R_{18}$ are independently hydrogen, hydroxyl, halide, alkyl, alkoxy, amino, alkylamino, or dialkylamino.

The compounds of formula (II) include:

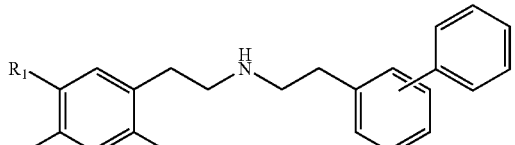
(II)

wherein $R_1$, $R_2$, and $R_3$ are independently hydrogen, hydroxyl, halide, alkyl, aryl, alkoxy, aryloxy, amino, alkylamino, or dialkylamino.

As used herein, the term "halide" unless otherwise specified refers to a substituent that is a Group VIIA element, preferably fluorine, chlorine, bromine, or iodine.

As used herein, the term "alkyl" unless otherwise specified refers to both straight chains alkyls that have the formula —$(CH_2)_xCH_3$ where x is from 0 to 9, and branched chain alkyls that have the formula as defined above for straight chain alkyls, except that one or more $CH_2$ groups are replaced by CHW groups where W is an alkyl side chain. Exemplary alkyl groups include, without limitation, methyl, ethyl, propyl, 1-methylpropyl, 2-methylpropyl, butyl, t-butyl, pentyl, hexyl, heptyl, octyl, nonyl, decyl, etc. Alkyl groups that are substituents of a larger R-group, e.g., alkoxy, alkylester, alkylamino, alkylamido, etc. can be an alkyl group as defined above.

As used herein, the term "alkenyl", unless otherwise specified, refers to both straight chain alkenyls that have the formula —(CH$_2$)$_{xa}$CH=CH(CH$_2$)$_{xb}$CH$_3$ where xa and xb each are from 0 to 7 and (xa+xb) is not more than about 7; and branched chain alkenyls have the formula as defined above for straight chain alkenyl, except that one or more CH$_2$ groups are replaced by CHW groups or a CH group is replaced by a CW group, where W is an alkyl side chain. Exemplary alkenyl groups include, without limitation, —CHCHC(CH$_3$)$_3$, and —(CHCH)$_n$CH$_3$ where n is an integer from 1 to 4. Alkenyl groups also include those possessing multiple alkene double bonds, such as di-enes, tri-enes, etc. Alkenyl groups that are substituents of a larger R-group can be an alkenyl group as defined above.

As used herein, the term "aryl" refers to single, multiple, or fused ring structures containing one or more aromatic or heteroaromatic rings. Exemplary aryls include, without limitation, phenyls, indenes, pyrroles, imidazoles, oxazoles, pyrrazoles, pyridines, pyrimidines, pyrrolidines, piperidines, thiophenes, furans, napthals, bi-phenyls, tri-phenyls, and indoles. The aromatic or heteroaromatic rings can include mono-, di-, or tri-substitutions of the ring located at the ortho, meta, or para positions. Preferred aryls include, without limitation:

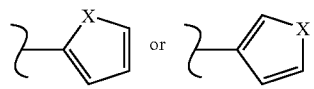

where X is oxygen, sulfur, or nitrogen,

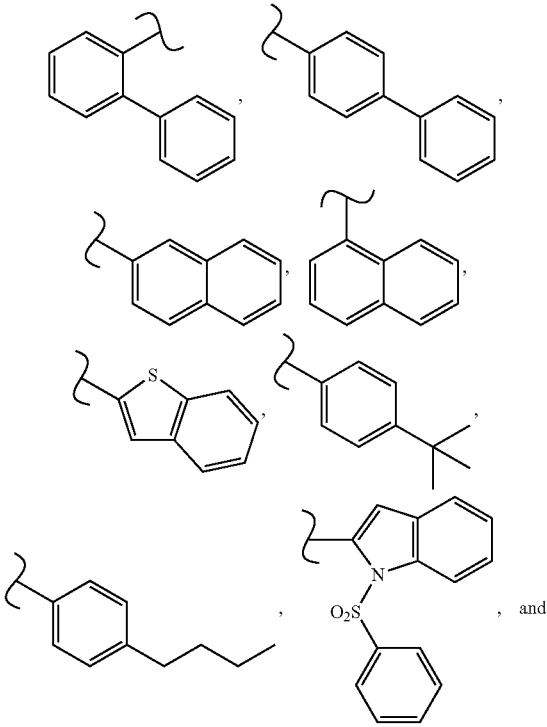

, and

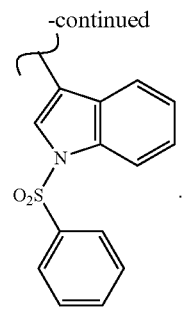

Aryl groups that are substituents of a larger R-group, e.g., aryloxy, arylamino, arylalkyl, arylamido, etc., can be an aryl group of the type defined above.

The compounds of the present invention can be prepared as either a racemic mixture, which includes both (+) and (−) stereoisomers, or as a substantially pure stereoisomer. By racemic mixture, it is intended that the mixture contain an approximately 1:1 ratio of the (+) and (−) isomers. By substantially pure, it is intended that one isomer is prepared such that it is at least about 85 percent pure, more preferably at least about 90 pure, most preferably at least about 95, 96, 97, 98, or 99 percent pure relative to its stereoisomer. Thus, as an example, a preparation that includes 85 or more percent by weight of a (+)-isomer and 15 percent or less percent by weight of the corresponding (−)-isomer is considered substantially pure for the (+)-isomer and substantially free of the (−)-isomer. Purification of stereoisomers one from another can be performed using conventional high performance liquid chromatography techniques designed to separate the stereoisomers or by using substantially pure starting materials or intermediates, thereby affording substantially pure final products.

When R$_9$ is

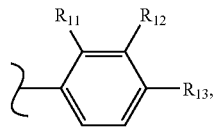

preferred compounds of the present invention are characterized by mono-substitution of the phenyl ring (of the R$_9$ substitutent). Thus, when R$_{13}$ is a substituent other than hydrogen, R$_{11}$ and R$_{12}$ are both hydrogen; when R$_{12}$ is a substituent other than hydrogen, R$_{11}$ and R$_{13}$ are both hydrogen; and when R$_{11}$ is a substituent other than hydrogen, R$_{12}$ and R$_{13}$ are both hydrogen.

Preferred compounds of the present invention include the following:

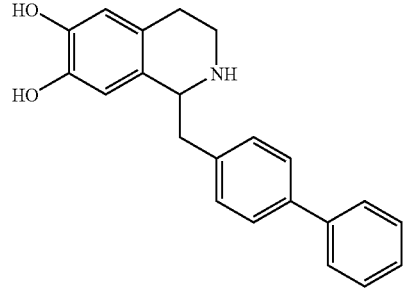

6,7-bis-hydroxy-1-biphenyl-4-ylmethyl-1,2,3,4-tetrahydro-isoquinoline;
1-(4-benzo[b]thiophen-2-yl-benzyl)-1,2,3,4-tetrahydro-isoquinoline-6,7-diol;
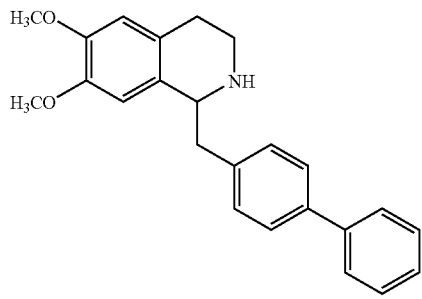
6,7-bis-methoxy-1-biphenyl-4-ylmethyl-1,2,3,4-tetrahydro-isoquinoline;
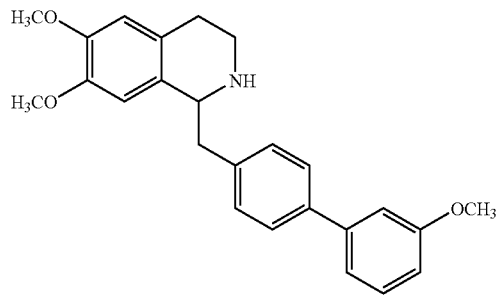
6,7-dimethoxy-1-(3'-methoxy-biphenyl-4-ylmethyl)-1,2,3,4-tetrahydro-isoquinoline;
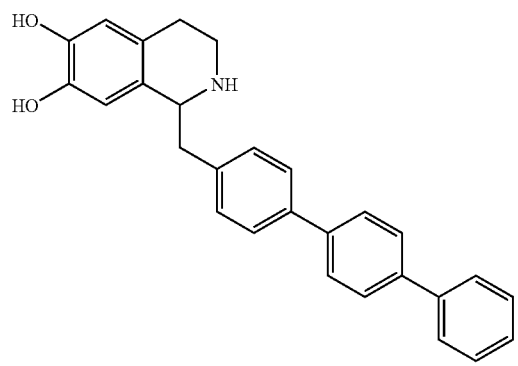
1-[1,1';4',1"]terphenyl-4-ylmethyl-1,2,3,4-tetrahydro-isoquinoline-6,7-diol;
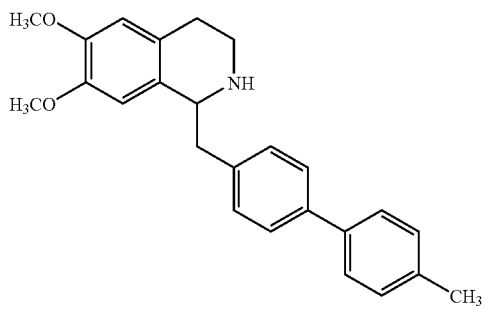
6,7-dimethoxy-1-(4'-methyl-biphenyl-4-ylmethyl)-1,2,3,4-tetrahydro-isoquinoline;
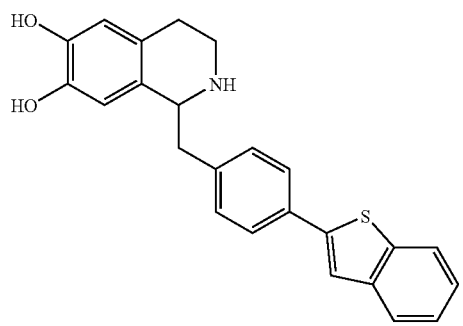
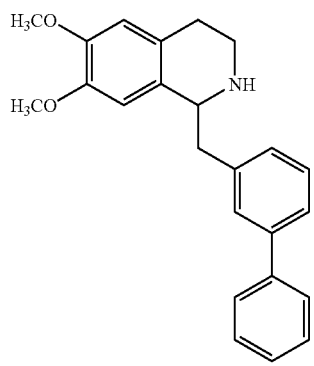

1-biphenyl-3-ylmethyl-6,7-dimethoxy-1,2,3,4-tetrahydro-isoquinoline; and

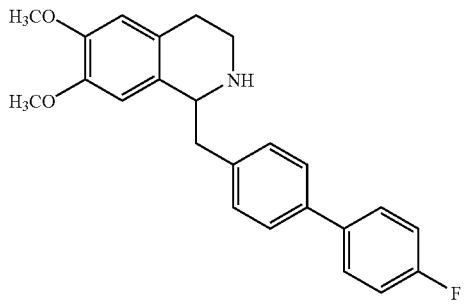

1-(4'-fluoro-biphenyl-4-ylmethyl)-6,7-dimethoxy-1,2,3,4-tetrahydro-isoquinoline.

The compounds of the present invention can be in the form of neutral compounds or in the form of salts. Pharmaceutically acceptable salts include those formed with free amino groups or with free carboxyl groups. Exemplary amino-salts include, without limitation, hydrochloric, hydrobromic, phosphoric, acetic, oxalic, tartaric acids, etc. Exemplary carboxyl-salts include, without limitation, sodium, potassium, ammonium, calcium, ferric hydroxides, isopropylamine, triethylamine, 2-ethylamino ethanol, histidine, procaine, etc. Because the structure of formulae (I) and (II) may include an available nitrogen (i.e., in the N-hetero ring of formula (I) or the secondary amino group of formula (II)), amino-salts are preferred. Suitable salts can be prepared in accordance with known procedures.

Generally, the compounds of the present invention can be synthesized according to the procedures shown in the synthesis schemes below and other widely known reaction schemes for effecting a substitution of one group for another on an intermediate compound.

Compounds of the present invention where $R_9$ is phenyl, $R_{11}$ and $R_{12}$ are hydrogen, and $R_{13}$ is alkyl, arylalkyl, alkenyl, alkoxy, aryloxy, amino, alkylamino, dialkylamino, arylamino, aryl, cyclohexyl, or

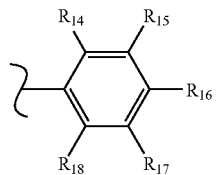

as described above, can be prepared according to Scheme 1 below.

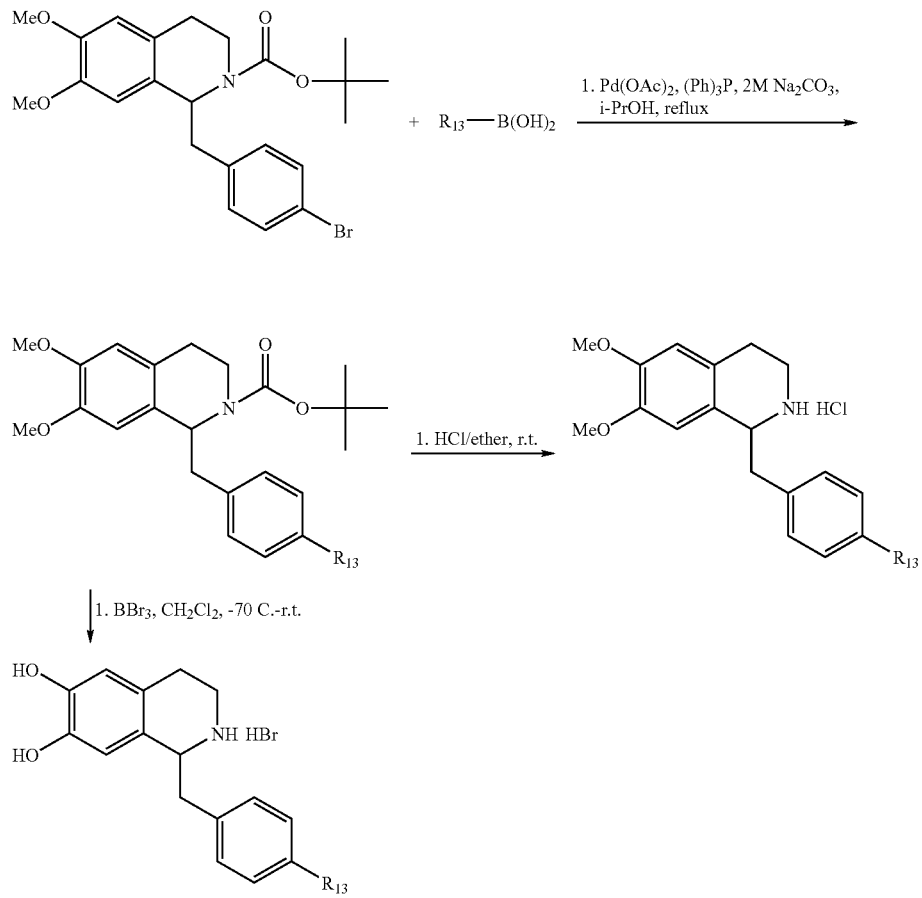

To prepare compounds of the present invention where $R_9$ is phenyl and either $R_{11}$ or $R_{12}$ is alkyl, arylalkyl, alkenyl, alkoxy, aryloxy, amino, alkylamino, dialkylamino, arylamino, aryl, cyclohexyl, or

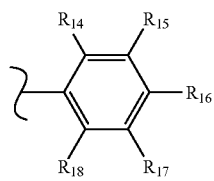

as described above, an analog of the starting compound shown in Scheme 1 can be used where the Br group (to be displaced) is bound to the phenyl group of $R_9$ at either the $R_{11}$ (ortho) position or the $R_{12}$ (meta) position, respectively (see Example 12 infra).

Compounds of the present invention where $R_9$ is phenyl and $R_{13}$ is alkyl, arylalkyl, alkenyl, alkoxy, aryloxy, amino, alkylamino, dialkylamino, arylamino, aryl, cyclohexyl, or

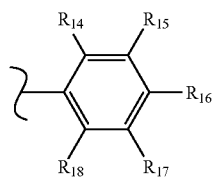

as described above, and where $R_6$ and $R_7$ together are —$(CH_2)_4$— forming a ring structure fused with the N-hetero ring of (I), can be prepared according to Scheme 2 below.

Scheme 2

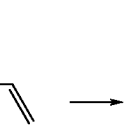

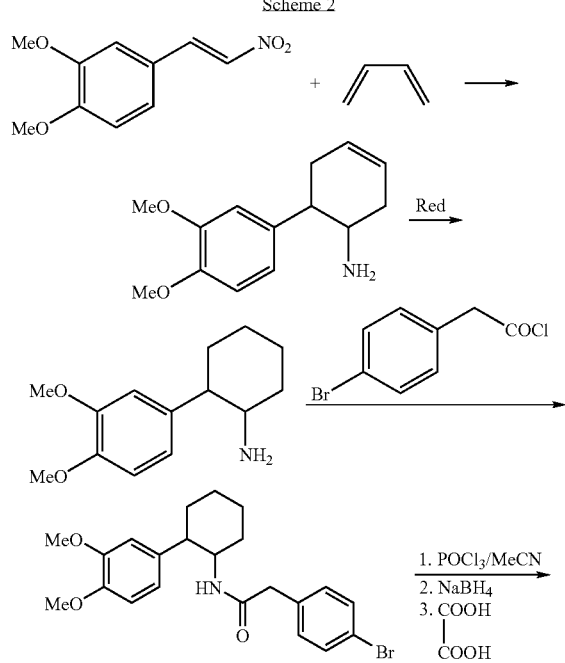

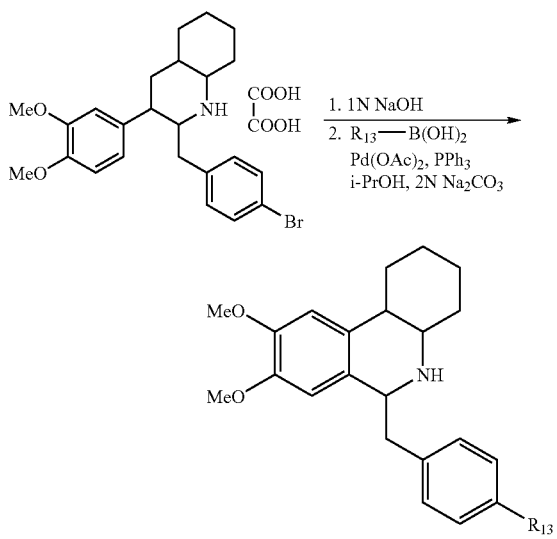

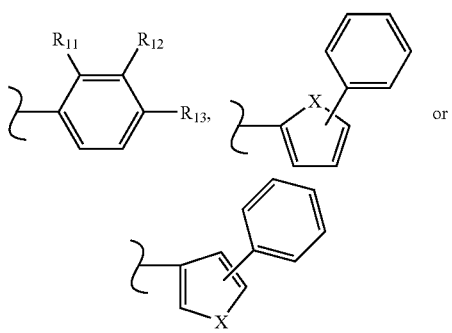

Compounds of the present invention where $R_9$ is

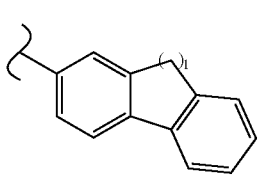

where X is oxygen, sulfur, or nitrogen,

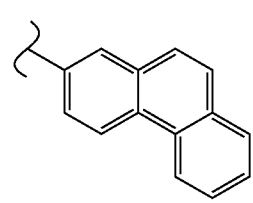

where l is 1 or 2, or as described above, can be synthesized according to Scheme 3 below.

Scheme 3

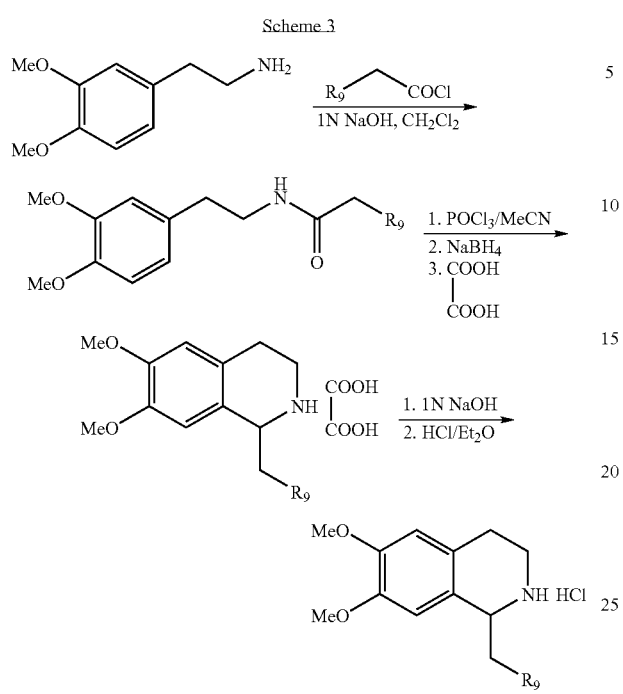

Compounds of the present invention where $R_1$ and $R_{10}$ together are —$(CH_2)_2$— forming a ring structure fused with both the benzene ring and the N-hetero ring of (I), can be prepared as shown in Scheme 4 below.

Scheme 4

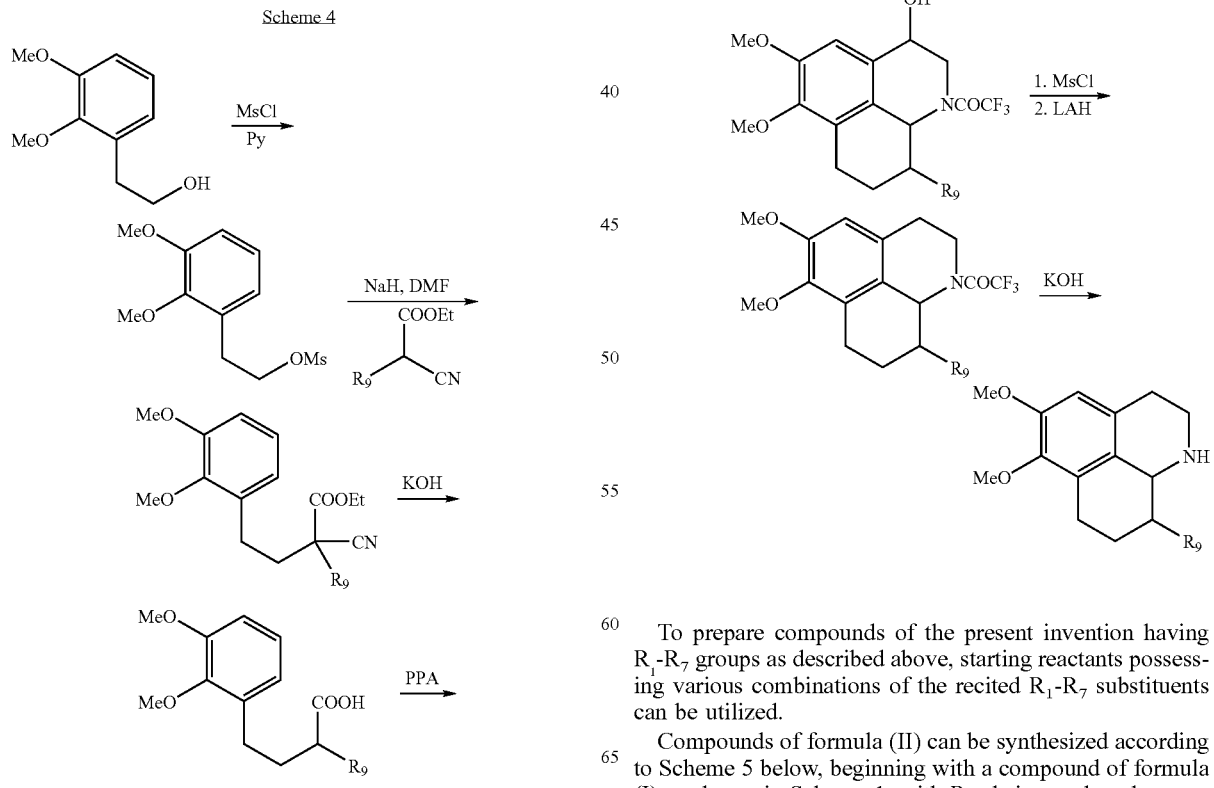

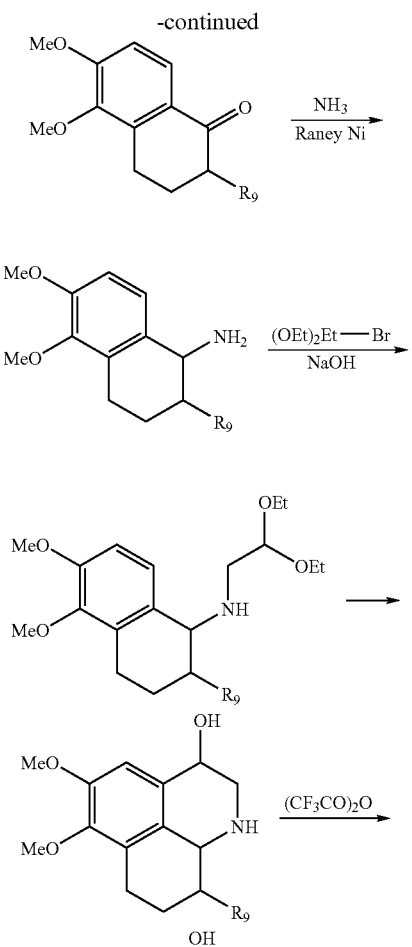

To prepare compounds of the present invention having $R_1$-$R_7$ groups as described above, starting reactants possessing various combinations of the recited $R_1$-$R_7$ substituents can be utilized.

Compounds of formula (II) can be synthesized according to Scheme 5 below, beginning with a compound of formula (I) as shown in Scheme 1, with $R_{13}$ being a phenyl group.

Scheme 5

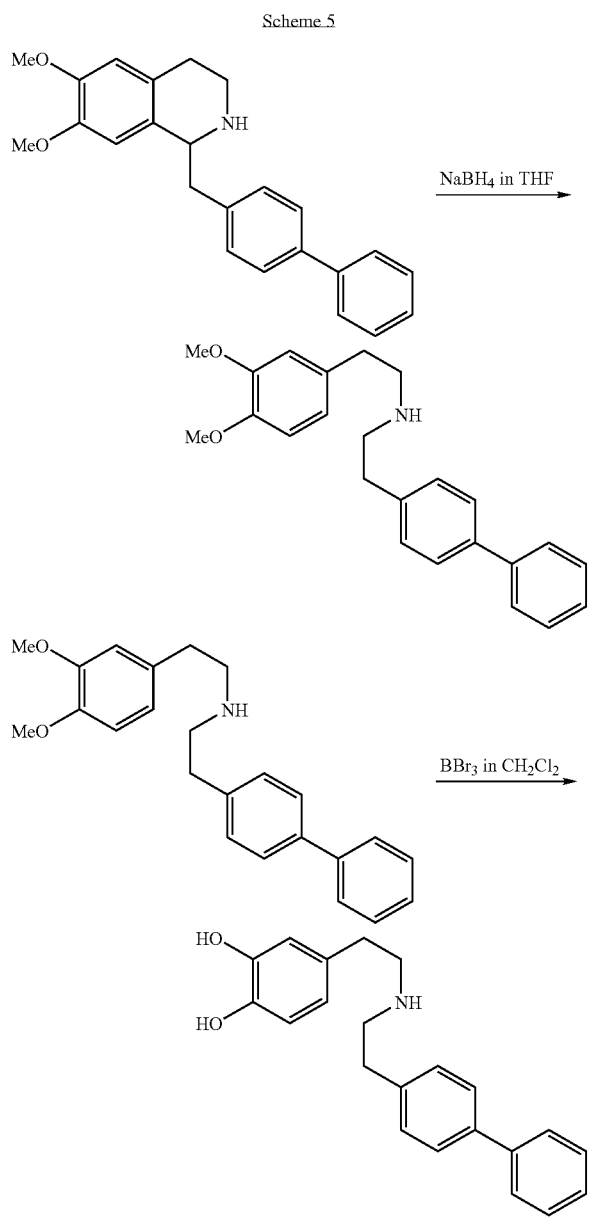

Having prepared the compounds of the present invention, they are capable of being introduced into a pharmaceutically acceptable carrier to afford a pharmaceutical composition of the present invention. The pharmaceutical composition can also include suitable excipients, or stabilizers, and can be in solid or liquid form such as, tablets, capsules, powders, solutions, suspensions, or emulsions. Typically, the composition will contain from about 0.01 to 99 percent by weight, preferably from about 10 to 75 percent by weight of active compound(s), together with the carrier and other inert ingredients.

The solid unit dosage forms can be of the conventional type. The solid form can be a capsule, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The compounds of the present invention may also be administered in injectable dosages by solution or suspension of these materials in a physiologically acceptable diluent with the pharmaceutical carrier. Such carriers include sterile liquids, such as water and oils, with or without the addition of surfactant(s), adjuvant(s), excipients(s), or stabilizer(s). Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Depending upon the treatment being effected, the compounds of the present invention can be administered orally, topically, transdermally, parenterally, subcutaneously, intravenously, intramuscularly, intraperitoneally, by intranasal instillation, by intracavitary or intravesical instillation, by inhalation, intravaginally, intracranially (e.g., by cannula), intraocularly, intraarterially, intralesionally, or by application to mucous membranes, such as, that of the nose, throat, and bronchial tubes. Other routes of administration can be identified by those of ordinary skill in the art.

The compounds of the present invention are particularly useful in the treatment or prevention of various forms of cancer, including without limitation, brain cancer, lung cancer, breast cancer, prostate cancer, and cervical cancer. It is believed that other forms of cancer will likewise be treatable or preventable upon administration of the compounds or compositions of the present invention to a patient. Without being bound by theory, it is believed that the compounds of the present invention selectively disruptive to cancer cells, causing disruption of cellular metabolism (possibly by destroying mitochondria in the cancer cells) and eventually ablation of cancer cells. Significantly, harm to normal cells is minimized because the cancer cells are susceptible to disruption at much lower concentrations of the compounds of the present invention.

Thus, a further aspect of the present invention relates to a method of destroying a target cell that includes: contacting a target cell, preferably a cancer cell, with a compound of the present invention under conditions effective to destroy the target cell.

A still further aspect of the present invention relates to a method of treating or preventing a cancerous condition that includes: administering an effective amount of a compound of the present invention to a patient under conditions to treat an existing cancerous condition or prevent development of a cancerous condition. To prevent development of a cancerous condition, a precancerous condition can be treated.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. When the compounds or pharmaceutical compositions of the present invention are administered to treat or prevent a cancerous condition, the pharmaceutical composition can also contain, or can be administered in conjunction with, other therapeutic agents or treatment regimen presently known or hereafter developed for the treatment of various types of cancer. Examples of other therapeutic agents or treatment regimen include, without limitation, radiation therapy, chemotherapy, surgical intervention, and combinations thereof.

Compositions within the scope of this invention include all compositions wherein the compound of the present invention is contained in an amount effective to achieve its intended purpose. While individual needs may vary, determination of optimal ranges of effective amounts of each component is within the skill of the art. Typical dosages comprise about 0.01 to about 100 mg/kg·body wt. The preferred dosages comprise about 0.1 to about 100 mg/kg·body wt. The most preferred dosages comprise about 1 to about 100 mg/kg·body wt. Treatment regimen for the administration of the compounds of the present invention can also be determined readily by those with ordinary skill in art.

EXAMPLES

The following examples are intended to illustrate, but by no means are intended to limit, the scope of the present invention as set forth in the appended claims.

Example 1

Preparation of the Racemic 6,7-bis-hydroxy-1-biphenyl-4-ylmethyl-1,2,3,4-tetrahydro-isoquinoline hydrochloride The intermediate 2-biphenyl-4-yl-N-[2-(3,4-bis-benzyloxy-phenyl)-ethyl]-acetamide (1) was prepared as follows: To a stirred solution of 2.85 g (7.7 mmol) of 3,4-dibenzyloxyphenethyl amine and 1.49 g (7 mmol) of 4-biphenylacetic acid in 20 ml of anhydrous dimethylformamide at 0° C., 2.5 ml (17.7 mmoles) of triethyl amine was added dropwise and then 1.4 ml (7.7 mmol) of diethyl cyanophosphonate (90% purity) was added dropwise. The reaction mixture was stirred for 22 hours and allowed to reach room temperature, and then it was poured into 300 ml of water. The precipitated solid was separated on a glass filter funnel, washed with water (3×70 ml), and air-dried overnight. This solid was recrystallized using hexanes/ethanol mixture to provide 3.1 g (84%) of grayish crystals, mp 142-144° C.

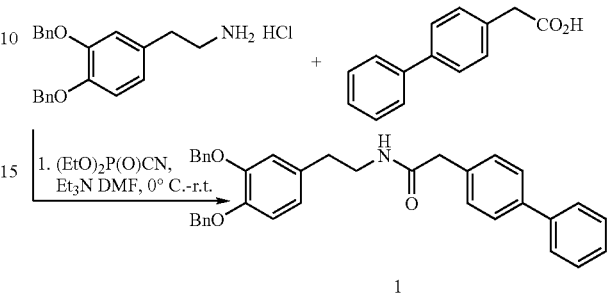

6,7-bis-benzyloxy-1-biphenyl-4-ylmethyl-1,2,3,4-tetrahydro-isoquinoline hydrochloride (2) was prepared as follows: A stirred solution of 3 g (5.69 mmol) of 2-biphenyl-4-yl-N-[2-(3,4-bis-benzyloxy-phenyl)-ethyl]-acetamide and 5.6 ml (60 mmol) of phosphorus oxychloride in 25 ml of anhydrous acetonitrile was refluxed for 20 hours. The reaction solution was evaporated under reduced pressure and the residue was dissolved in 25 ml of methanol. To this stirred solution at 0° C., 2.27 g (60 mmol) of sodium borohydride was added portionwise. The stirred reaction mixture was allowed to reach room temperature overnight and then it was poured in 150 ml of 10% aqueous HCl solution. The precipitate was collected on a glass filter funnel, washed with water (3×50 ml), and air-dried overnight. The solid was recrystallized using ether/methanol mixture to provide 2.56 g (82%) of off-white crystals, mp 187-189° C.

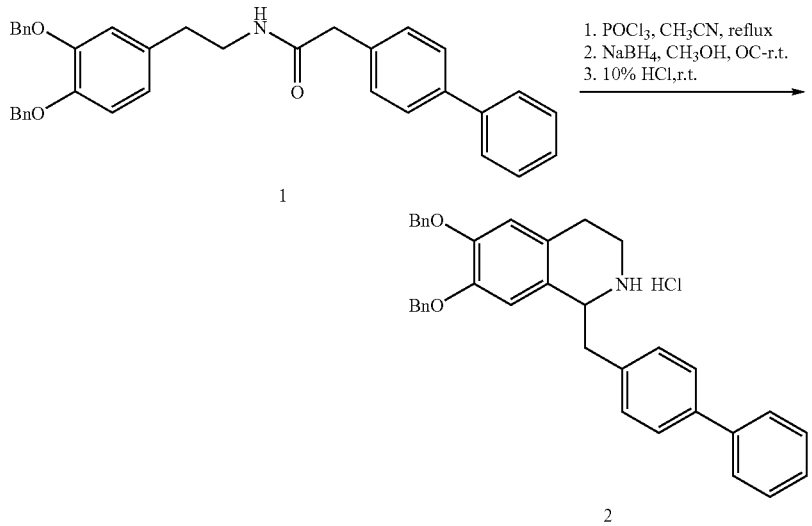

6,7-bis-hydroxy-1-biphenyl-4-ylmethyl-1,2,3,4-tetrahydro-isoquinoline hydrochloride (3) was prepared as follows: A stirred mixture of 2.5 g (4.56 mmol) of 6,7-bis-benzyloxy-1-biphenyl-4-ylmethyl-1,2,3,4-tetrahydro-isoquinoline hydrochloride in 10 ml of concentrated aqueous HCl solution/10 ml of methanol was refluxed for 10 hours. The solvents were evaporated under reduced pressure, the solid residue was mixed with 10 ml of ether and separated on a glass filter funnel, and then washed with ether (2×10 ml). This solid was recrystallized using ether/methanol mixture to give 1.3 g (78%) of off-white crystals, mp 208-210° C.

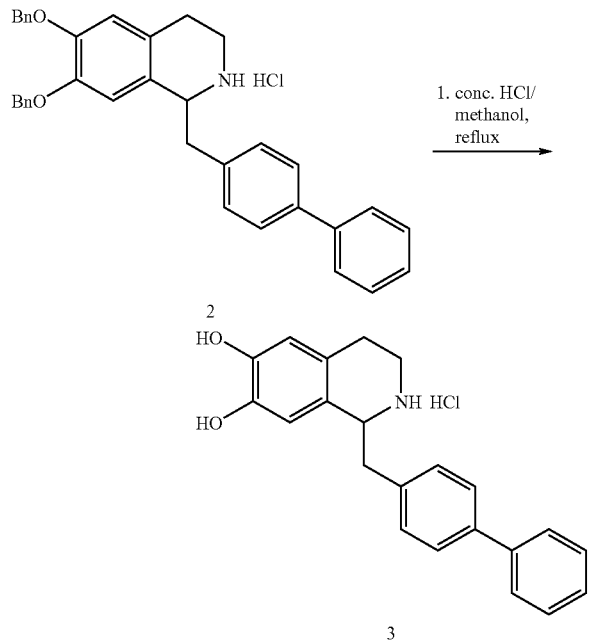

Example 2

Chiral Separation of 6,7-bis-hydroxy-1-biphenyl-4-ylmethyl-1,2,3,4-tetrahydro-isoquinoline hydrochloride The chiral separation of the racemic mixture prepared in Example 1 was done on HP 1100 HPLC system using reversed-phase ChromTech Chiral-AGP column (150×4 mm). The column was operated in isocratic mode at a rate of 0.9 mL/min using a mobil phase of 7% acetonitrile in 10 mM sodium phosphate buffer, pH 5.5.

Example 3

In vivo Testing of 6,7-bis-hydroxy-1-biphenyl-4-ylmethyl-1,2,3,4-tetrahydro-isoquinoline hydrochloride A rat model system was developed to examine the in vivo efficacy of the compounds of the present invention.

The first step was to produce a cell line with a marker gene. A rat C6 glioma cell line was selected and stably transfected with a beta galactosidase construct. These cells were cultured and prepared to be injected into the brain of adult Sprague-Dawley rats to simulate in vivo tumor development.

The animals were anesthetized and a cannula was placed into the brain. Approximately $5 \times 10^4$ glioma cells were injected through the cannula. The cannula was then attached to an osmotic mini pump containing one of three treatment solutions: Hanks Balanced Salts (HBSS), HBSS plus 10 μM BCNU or HBSS with 7 μM 6,7-bis-hydroxy-1-biphenyl-4-ylmethyl-1,2,3,4-tetrahydro-isoquinoline hydrochloride. The mini osmotic pump delivered 1 μl/hr for 7 days. With the tubing used to connect the pump, there was approximately a 10 hour delay for the treatment to reach the brain.

Figure 3:
FIG. 3 is an enlargement of FIG. 1E, illustrating that the transplanted glioma are virtually absent. Of interest, the brain tissue at the end of the cannula has substantially maintained its integrity despite the initial infiltration of the glioma cells and the subsequent drug administration.

As can be seen in FIGS. 1A-C and 1D, respectively, the presence of the glioma is quite noticeable within the control and BCNU-treated brains. In addition to labeling the glioma, the beta galactosidase reaction also labels the choroids plexus in the lateral ventricles (the dark blue vertical stripes in the 6,7-bis-hydroxy-1-biphenyl-4-ylmethyl-1,2,3,4-tetrahydro-isoquinoline hydrochloride treated brain). As can be seen, the tumor is well established in the control brain and the BCNU-treated brain by 7 days. In the 6,7-bis-hydroxy-1-biphenyl-4-ylmethyl-1,2,3,4-tetrahydro-isoquinoline hydrochloride treated brain, there is very little tumor present. The section with the largest extent of tumor visible in all of the cases was identified and the cross-sectional area of the tumor was measured. These results are displayed in FIG. 2. It is worth noting that these are cross-sectional areas and if volume were measured the differences between animals would be even greater. In some of the control brains the tumors had expanded to occupy nearly ¼ of the brain mass. The morphology of the hippocampus beneath the treatment cannula is shown in FIG. 3. Notice that there is very little pathology caused by the 6,7-bis-hydroxy-1-biphenyl-4-ylmethyl-1,2,3,4-tetrahydro-isoquinoline hydrochloride treatment. Thus, this compound causes a significant reduction in brain tumor size and it does not kill the normal brain tissue.

Example 4

In vitro Analysis of 6,7-bis-hydroxy-1-biphenyl-4-ylmethyl-1,2,3,4-tetrahydro-isoquinoline hydrochloride on Cancer Cell Lines Below are described a series of experiments that point to a potential mechanism concerning the mechanism of action of 6,7-bis-hydroxy-1-biphenyl-4-ylmethyl-1,2,3,4-tetrahydro-isoquinoline hydrochloride.

Figure 4A:
FIGS. 4A-B illustrate the activity of 6,7-bis-hydroxy-1-biphenyl-4-ylmethyl-1,2,3,4-tetrahydro-isoquinoline hydrochloride (MMGS-155) on U87 glioma. At 18 hr after treatment with 3 μM of 6,7-bis-hydroxy-1-biphenyl-4-ylmethyl-1,2,3,4-tetrahydro-isoquinol hydrochloride, the cells were fixed and stained with toluidine blue. Notice the presence of vacuoles in the treated cells (4B) but not the control cells (4A).
Figure 4B:
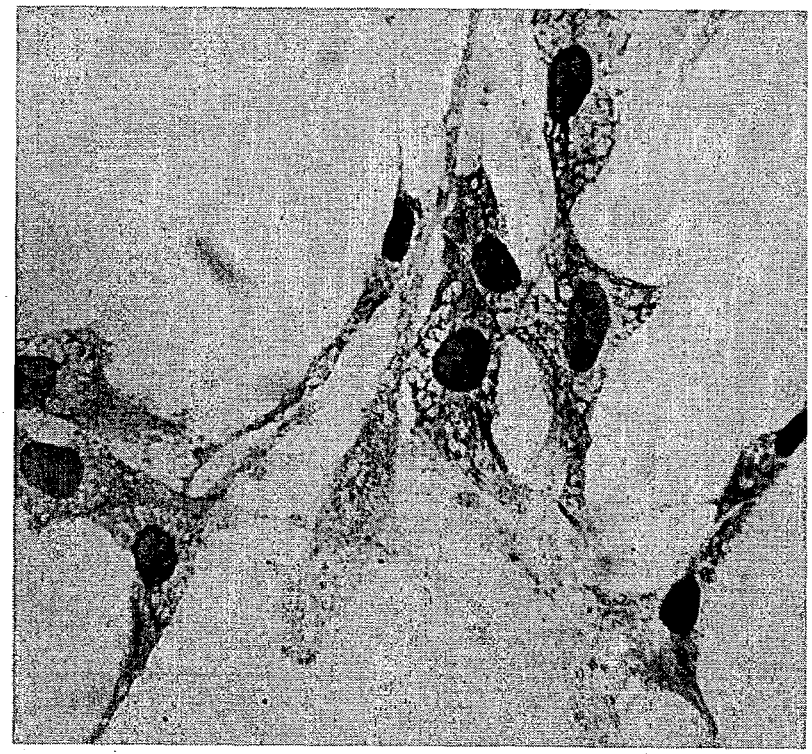
Figure 5A:
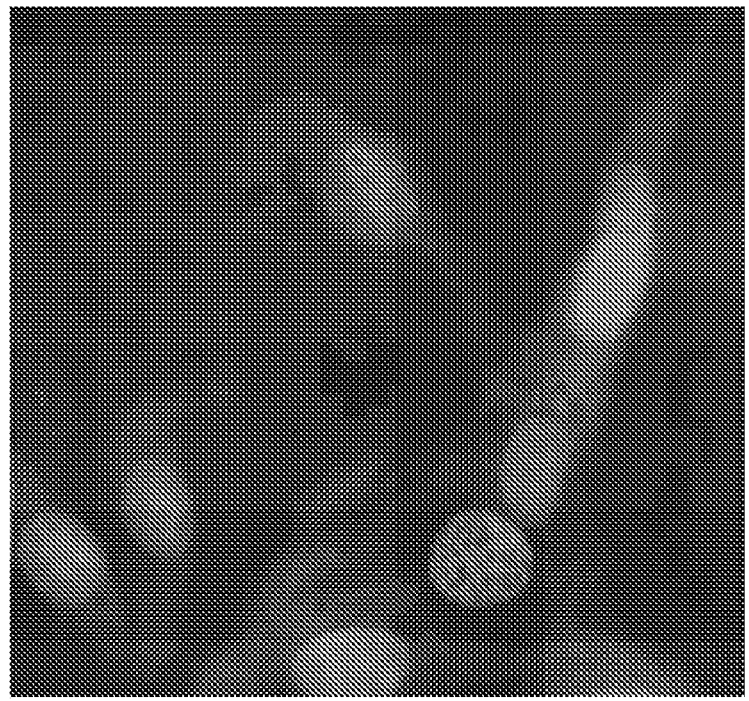
FIGS. 5A-B illustrate the morphological change in U87 glioma cells after 6,7-bis-hydroxy-1-biphenyl-4-ylmethyl-1,2,3,4-tetrahydro-isoquinoline hydrochloride treatment. U87 glioma cells were treated with 5 μM 6,7-bis-hydroxy-1-biphenyl-4-ylmethyl-1,2,3,4-tetrahydro-isoquinoline hydrochloride and at 18 hr the cells were stained with Hoechst dye. The cells built many vacuoles in cytosol. This change can be seen as early as at 5 hr after treatment.
Figure 5B:
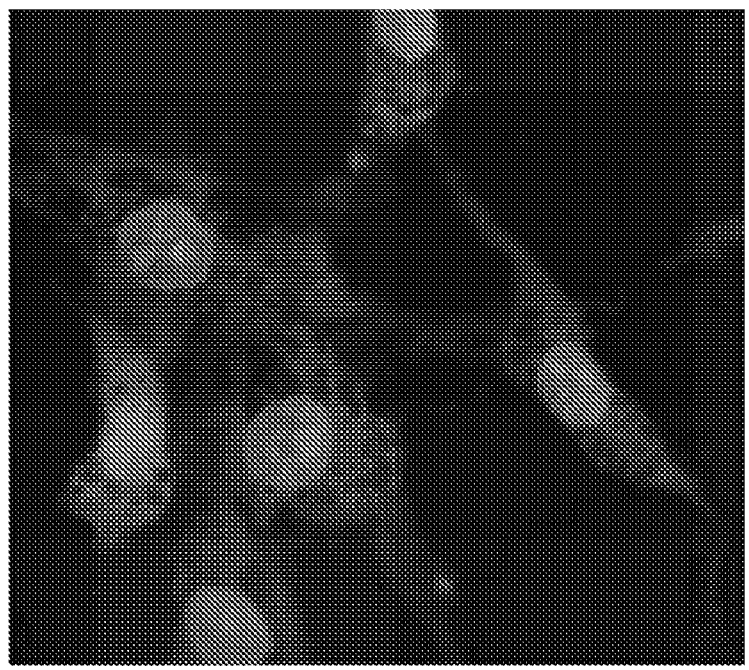
Figure 6A:
FIGS. 6A-B illustrate the morphological changes of glioma cells following 6,7-bis-hydroxy-1-biphenyl-4-ylmethyl-1,2,3,4-tetrahydro-isoquinoline hydrochloride treatment. The images were taken by electron microscope. The vacuoles observed in FIGS. 4B and 5B can be identified here as ruptured mitochondria (arrows).
Figure 6B:

When human glioma are treated with 6,7-bis-hydroxy-1-biphenyl-4-ylmethyl-1,2,3,4-tetrahydro-isoquinoline hydrochloride in culture, they develop vacuoles (FIGS. 4A-B). These vacuoles do not contain significant amounts of DNS (FIGS. 5A-B). When these treated cells were examined at the electron microscopic level (FIGS. 6A-B), these vacuoles appear to contain fragments of mitochondria. The cells treated with 6,7-bis-hydroxy-1-biphenyl-4-ylmethyl-1,2,3,4-tetrahydro-isoquinoline hydrochloride were closely examined and the striking feature of the vacuoles is contrasted by the absence of visible mitochondria. Thus, it appears that 6,7-bis-hydroxy-1-biphenyl-4-ylmethyl-1,2,3,4-tetrahydro-isoquinoline hydrochloride causes mitochondrial disruption and thereby destroys the cellular metabolism in the tumor cells.

Figure 7:
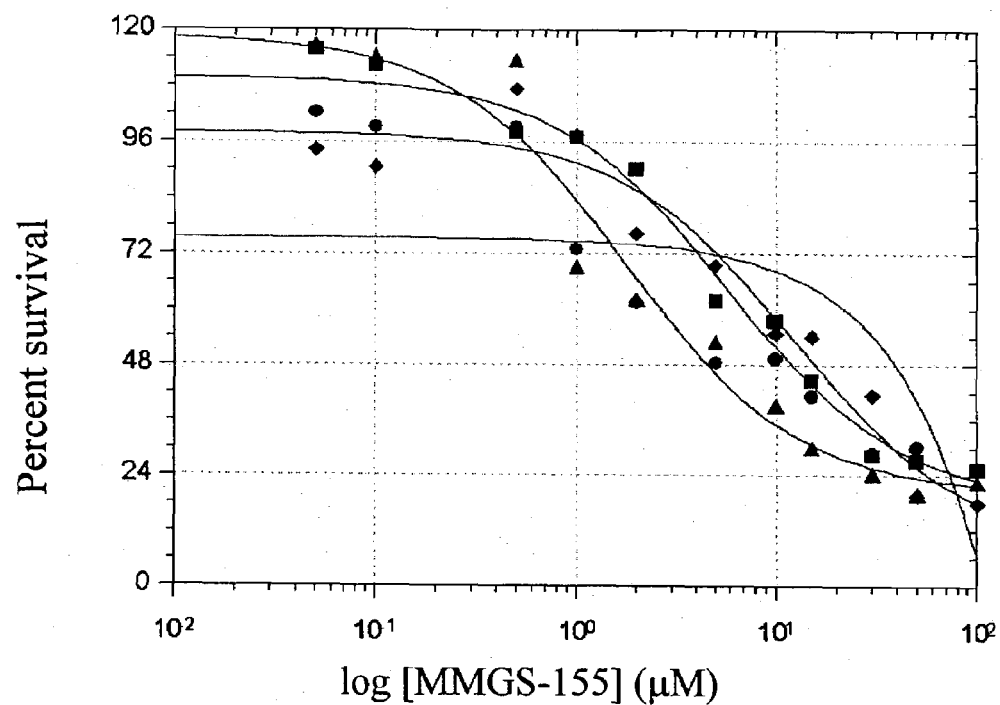
FIG. 7 is a graph illustrating the anti-proliferative activity of 6,7-bis-hydroxy-1-biphenyl-4-ylmethyl-1,2,3,4-tetrahydro-isoquinoline hydrochloride (MMGS-155) against cancer cell lines. The following cancer cell lines were treated with 6,7-bis-hydroxy-1-biphenyl-4-ylmethyl-1,2,3,4-tetrahydro-isoquinoline hydrochloride for 96 hr at various concentrations: MCF7 (breast cancer, •); A549 (lung epithelial cancer, ■); HeLa (cervix cancer, ▲); LnCap (prostate cancer, ♦). Cell proliferation was measured and $EC_{50}$ values were estimated. 6,7-bis-hydroxy-1-biphenyl-4-ylmethyl-1,2,3,4-tetrahydro-isoquinoline hydrochloride showed activity on all of the tested cancer cell lines.

Given the above results, 6,7-bis-hydroxy-1-biphenyl-4-ylmethyl-1,2,3,4-tetrahydro-isoquinoline hydrochloride was tested on a number of different types cancer cell lines as shown in FIG. 7. In every type of cancer tested to date, including brain cancer (glioma and glioblastoma), breast cancer, lung epithelial cancer, cervical cancer, and prostate cancer cell lines, 6,7-bis-hydroxy-1-biphenyl-4-ylmethyl-1,2,3,4-tetrahydro-isoquinoline hydrochloride has killed the cancer cells in culture with an $LD_{50}$ of approximately 3 μM.

Figure 8:
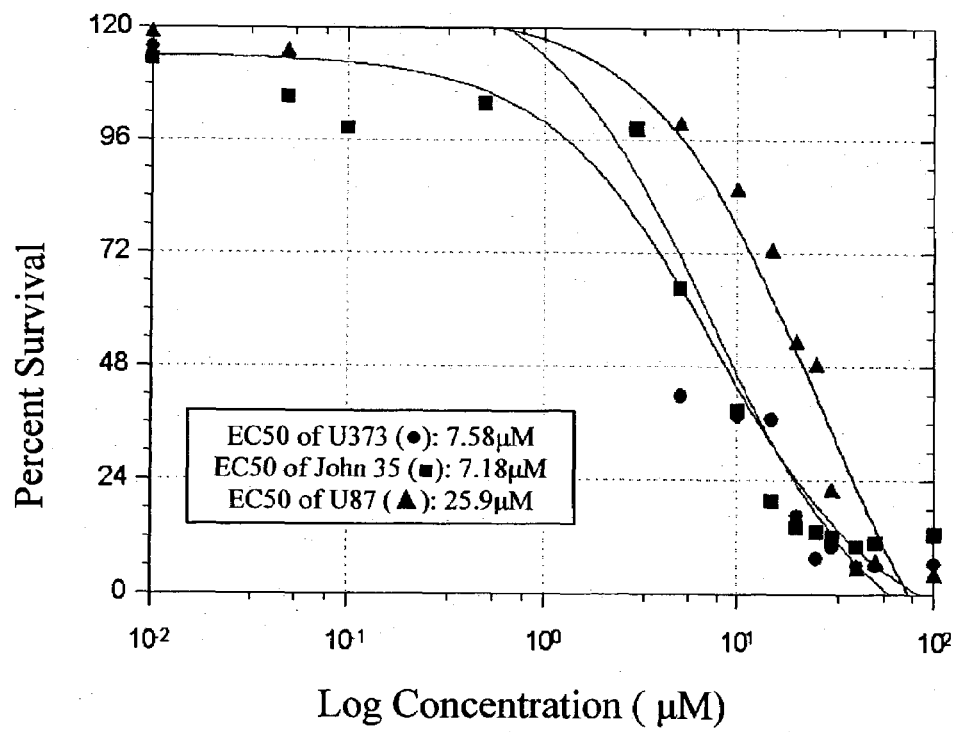
FIG. 8 is a graph illustrating the anticancer activity of 6,7-bis-hydroxy-1-biphenyl-4-ylmethyl-1,2,3,4-tetrahydro-isoquinoline hydrochloride on several different human glioblastoma cell lines.

With specific reference to glioblastoma cell lines, 6,7-bis-hydroxy-1-biphenyl-4-ylmethyl-1,2,3,4-tetrahydro-isoquinoline hydrochloride was effective in killing those cell lines (FIG. 8).

Example 5

Figure 9A:
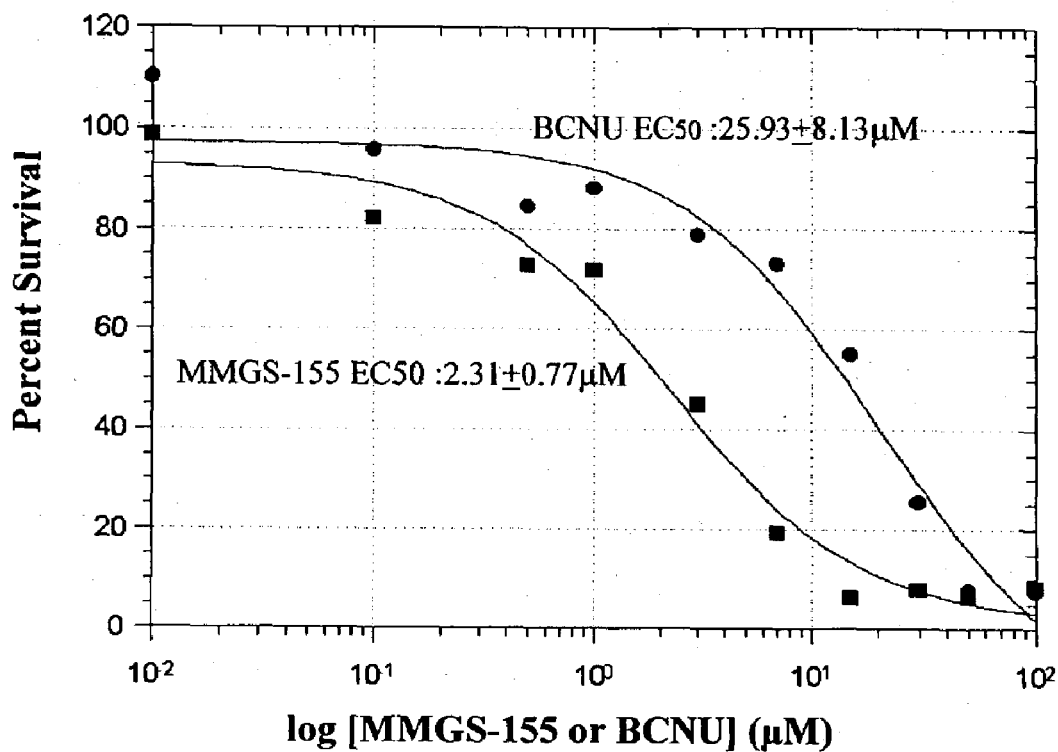
FIGS. 9A-B illustrate the comparision of anti-proliferative activity of 6,7-bis-hydroxy-1-biphenyl-4-ylmethyl-1,2,3,4-tetrahydro-isoquinoline hydrochloride (MMGS-155) and BCNU against C6 glioma cells.

Differential Effect of 6,7-bis-hydroxy-1-biphenyl-4-ylmethyl-1,2,3,4-tetrahydro-isoquinoline hydrochloride on C6 Glioma Cells and Normal Brain Cells To further assess the differential effect of 6,7-bis-hydroxy-1-biphenyl-4-ylmethyl-1,2,3,4-tetrahydro-isoquinoline hydrochloride on cancer cells and normal cells, in vitro analyses were performed using 6,7-bis-hydroxy-1-biphenyl-4-ylmethyl-1,2,3,4-tetrahydro-isoquinoline hydrochloride and BCNU. C6 glioma cells were treated with varying doses of 6,7-bis-hydroxy-1-biphenyl-4-ylmethyl-1,2,3,4-tetrahydro-isoquinoline hydrochloride and BCNU for 96 hr and the survival rate of the C6 glioma cells was determined. As shown in FIG. 9A, 6,7-bis-hydroxy-1-biphenyl-4-ylmethyl-1,2,3,4-tetrahydro-isoquinoline hydrochloride possesses an $EC_{50}$ of 2.31±0.77 μM whereas BCNU possesses an $EC_{50}$ of 25.93±8.13 μM. Thus, confirming earlier results, 6,7-bis-hydroxy-1-biphenyl-4-ylmethyl-1,2,3,4-tetrahydro-isoquinoline hydrochloride is an order of magnitude more potent than BCNU.

Figure 9B:
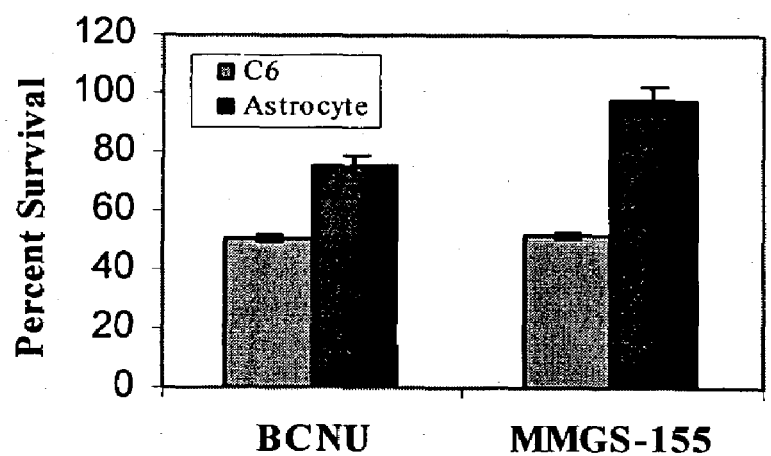

Even more compelling, however, is the greater specificity that 6,7-bis-hydroxy-1-biphenyl-4-ylmethyl-1,2,3,4-tetrahydro-isoquinoline hydrochloride has for the C6 cells over primary cultured cortical astrocytes. As shown in FIG. 9B, at $EC_{50}$ concentrations for the C6 gliomas, 6,7-bis-hydroxy-1-biphenyl-4-ylmethyl-1,2,3,4-tetrahydro-isoquinoline hydrochloride caused only minimal destruction to astrocytes whereas BCNU caused significant destruction to astrocytes. The $EC_{50}$ concentration of 6,7-bis-hydroxy-1-biphenyl-4-ylmethyl-1,2,3,4-tetrahydro-isoquinoline hydrochloride for astrocytes was an order of magnitude higher ($EC_{50}$=27.29±5.29 μM). Thus, 6,7-bis-hydroxy-1-biphenyl-4-ylmethyl-1,2,3,4-tetrahydro-isoquinoline hydrochloride is a cytotoxic agent that not only has a broad range of activity, as demonstrated in Example 6, but also selectively targets cancer cells over normal cells.

Figure 10:
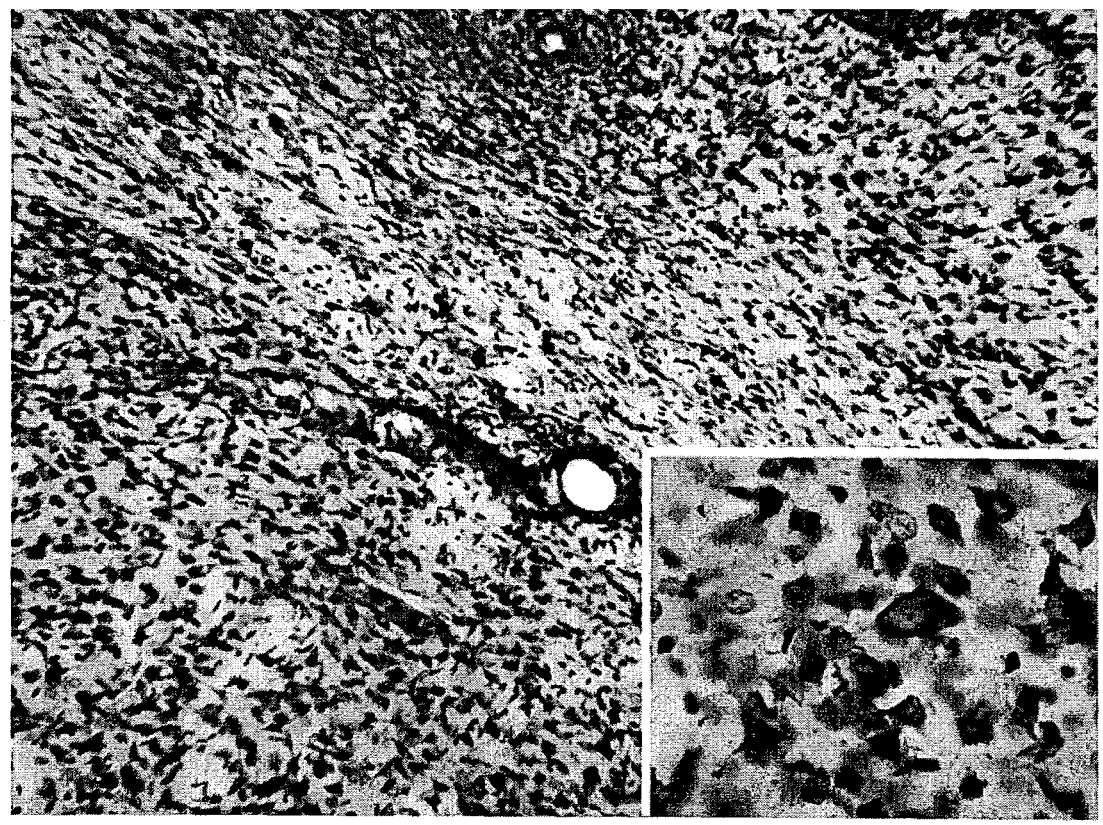
FIG. 10 illustrates the animal toxicity test of 6,7-bis-hydroxy-1-biphenyl-4-ylmethyl-1,2,3,4-tetrahydro-isoquinolin hydrochloride. The drug was delivered directly into the striatum of rats at a concentration of 5 μM, two times greater than the estimated $EC_{50}$ value. After implanting the mini-osmotic pump with MMGS-155 for five days, rats did not show any sign of brain damage. The rats were sacrificed, brain sections were investigated for any major tissue change in the brain. Brains were fixed in 4% paraformaldehyde and cut in sections and stained by the Nissl method.

To expand on these data, the in vivo effect of 6,7-bis-hydroxy-1-biphenyl-4-ylmethyl-1,2,3,4-tetrahydro-isoquinoline hydrochloride on healthy brain tissue was also measured. The drug was administered into the striatum of rats at 5 μM, which is approximately two times greater than the estimate $EC_{50}$ value. After implanting the mini-osmotic pump with MMGS-155 for five days, rats did not show any sign of brain damage. The rats were sacrificed, brain sections were investigated for any major tissue change in the brain. Brains were fixed in 4% paraformaldehyde and cut in sections and stained by the Nissl method. As shown in FIG. 10, the brain tissues appear normal.

Example 6

Preparation of the Racemic 1-[1,1';4',1'']Terphenyl-4-ylmethyl-1,2,3,4-tetrahydro-isoquinoline-6,7-diol hydrobromide The intermediate 1-(4-Bromo-benzyl)-6,7-dimethoxy-3,4-dihydro-1H-isoquinoline-2-carboxylic acid tert-butyl ester (11) was prepared as follows: To a stirred mixture of 2.76 g (6.92 mmoles) of 1-(p-bromobenzyl)-6,7,-dimethoxy-1,2,3,4-tetrahydro-isoquinoline hydrochloride and 1.81 g (1.2 mol.equiv.) of di-tert-butyldicarbonate in 100 ml of anhydrous tetrahydrofuran at room temperature, 2.3 ml (2.4 mol. equiv.) of triethyl amine was added. The reaction mixture was stirred at room temperature for 12 hours and then the solvent was evaporated under reduced pressure. The residue was partitioned between 150 ml of ethyl acetate and 100 ml of 5% citric acid aqueous solution. After shaking, the organic layer was washed with 100 ml of water and 100 ml of brine, and then dried ($Na_2SO_4$). The solvent was evaporated under reduced pressure and the remaining oil was crystallized by trituration with n-hexanes. The solid was recrystallized using n-hexanes\ethyl acetate mixture to furnish 2.59 g (81%) of off-white solid, mp 93-95° C.

6,7-Dimethoxy-1-[1,1';4'1'']terphenyl-4-ylmethyl-3,4-dihydro-1H-isoquinoline-2-carboxy acid tert-butyl ester (12) was prepared as follows: A mixture of 0.462 g (1 mmol) of 1-(4-Bromo-benzyl)-6,7-dimethoxy-3,4-dihydro-1H-isoquinoline-2-carboxylic acid tert-butyl ester and 0.297 g (1.5 mol. equiv.) of 4-biphenylboronic acid in 4 ml of isopropanol was stirred under argon at room temperature for 30 min. To this mixture, 1 mg (0.45 mol %) of Palladium(II) acetate, 4 mg (1.3 mol %) of triphenylphosphine, and 0.6 ml (1.2 mol. equiv.) of 2M sodium bicarbonate aqueous solution were added successively and the mixture was refluxed with stirring for 6 hours. The solvent was evaporated under reduced pressure and the residue was partitioned between 50 ml of ethyl acetate and 25 ml of 5% sodium hydroxide aqueous solution. After shaking, the organic layer was washed with water (25 ml) and brine (25 ml), and then dried with sodium sulfate. The solvent was evaporated under reduced pressure and the remaining oil was crystallized by trituration with n-hexanes. The solid was recrystallized using ethyl acetate\n-hexanes mixture to give 0.40 g (75%) of white solid, mp 153-155° C.

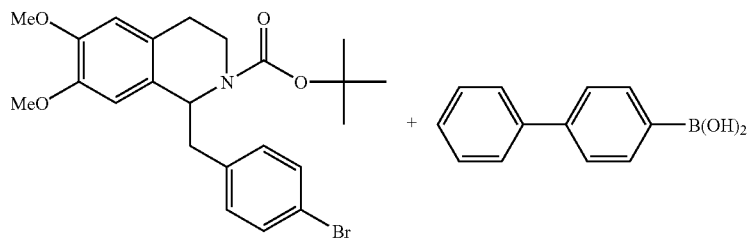

11

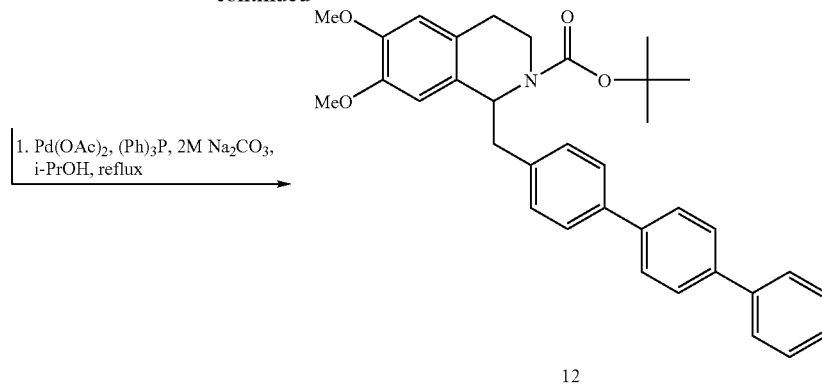

1-[1,1';4'1"]Terphenyl-4-ylmethyl-1,2,3,4-tetrahydro-isoquinoline-6,7-diol hydrobromide (13) was prepared as follows: To a stirred solution of 0.10 g (0.187 mmol) of 6,7-dimethoxy-1-[1,1';4',1"]terphenyl-4-ylmethyl-3,4-dihydro-1H-isoquino acid tert-butyl ester in 10 ml of anhydrous dichloromethane under argon at −70° C., 1 ml (5 mol. equiv.) of 1M boron tribromide solution in n-hexanes was added. The mixture was allowed to reach room temperature with stirring overnight and then the solvents were evaporated under reduced pressure. The residue was dissolved in 10 ml of methanol and, again, the solvent was evaporated under reduced pressure. The solid residue was mixed with 10 ml of ether, separated on a glass filter funnel, washed with ether (3×20 ml) to afford an off-white solid, 82 mg (90%), mp 262-264° C.

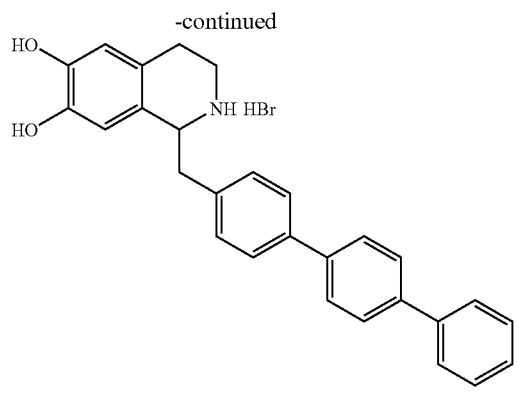

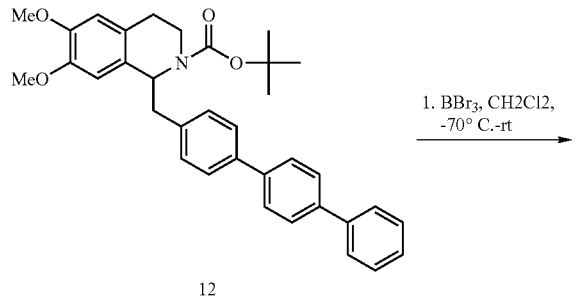

Example 7

Preparation of the 1-[1,1';4',1"]Terphenyl-4-ylmethyl-1,2,3,4-tetrahydro-isoquinoline-6,7-diol hydrobromide Isomers Stereoisomes of 1-[1,1';4',1"]Terphenyl-4-ylmethyl-1,2,3,4-tetrahydro-isoquinoline-6,7-diol hydrobromide will be prepared according to the reaction scheme below using (+)-menthyl chloroformate, which will allow stereoisomers of the intermediate compounds to be separately crystallized using standard conditions.

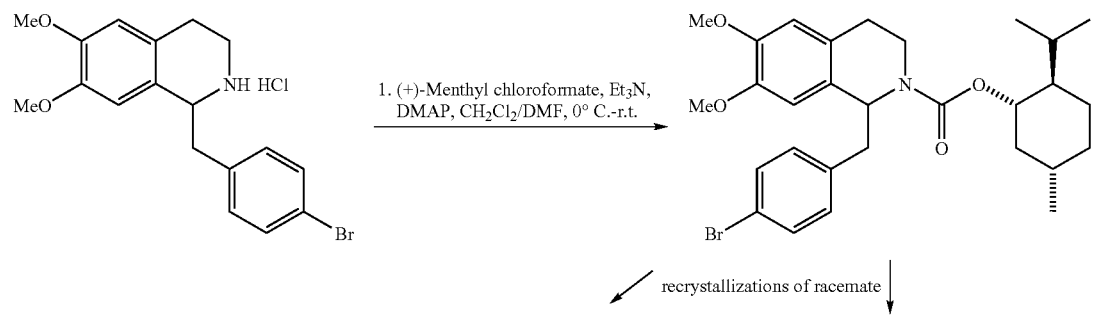

29
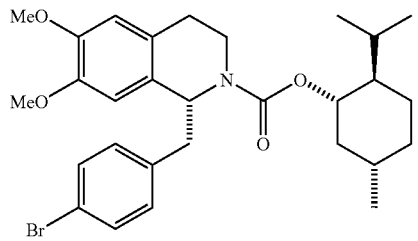
| 1. HBr in glacial AcOH, r.t.
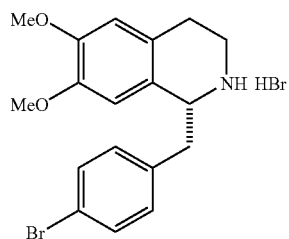
30
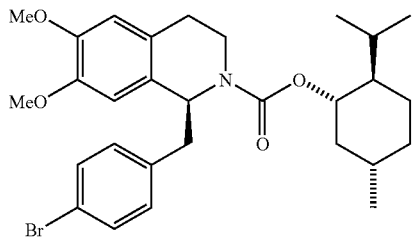
| 1. HBr in glacial AcOH, r.t.
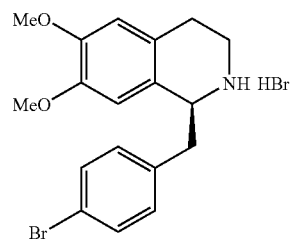
Once the stereoisomers have been separately crystallized, the (+)- and (−)-isomers can be used to prepare substantially pure compounds of the present invention as shown in the two reaction schemes shown below, where each isomer is substantially free of its corresponding isomer.
1.
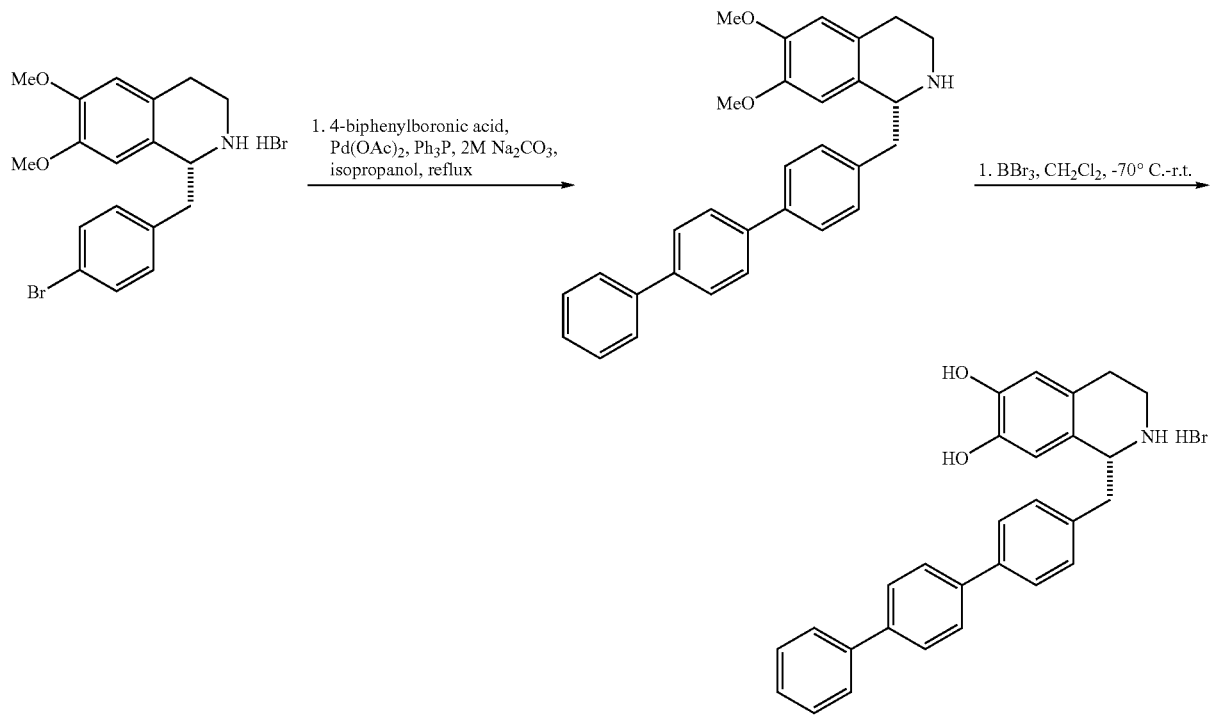

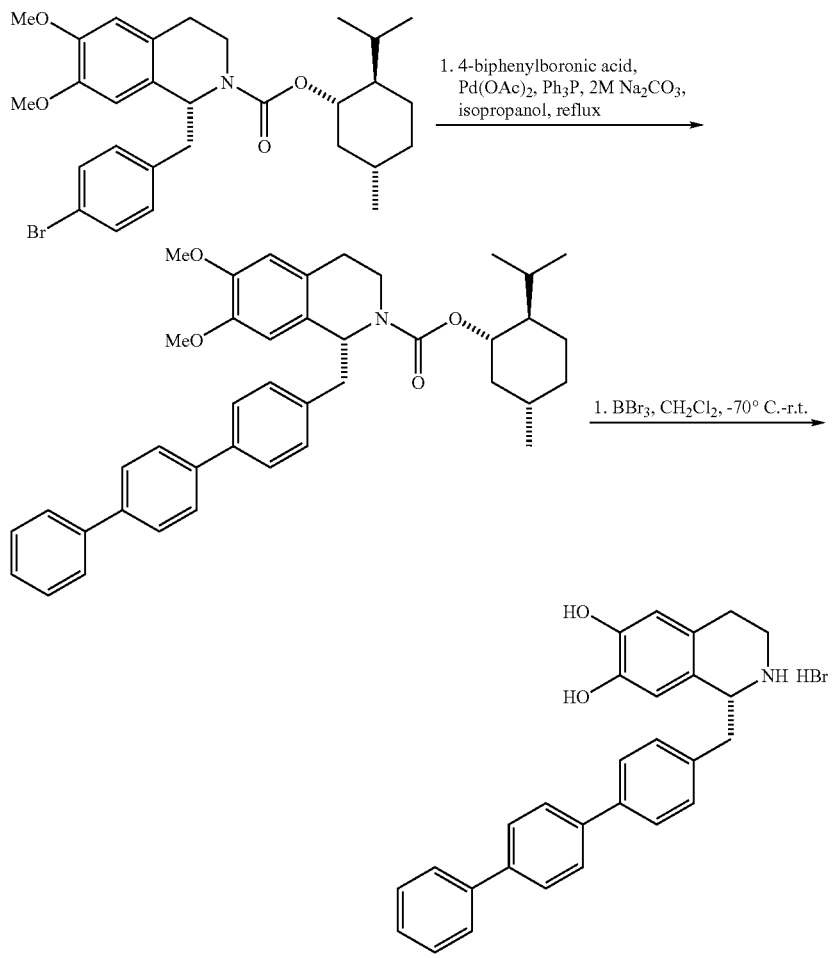

Example 8

Preparation of 1-(4-benzo[b]thiophen-2-yl-benzyl)-1,2,3,4-tetrahydro-isoquinoline-6,7-diol hydrobromide The intermediate 1-(4-Benzo[b]thiophen-2-yl-benzyl)-6,7-dimethoxy-8-methyl-3,4-dihydro-1-H-isoquinoline-2-carboxylic acid tert-butyl ester (21) was prepared as follows: A mixture of 0.462 g (1 mmol) of 1-(4-Bromo-benzyl)-6,7-dimethoxy-3,4-dihydro-1H-isoquinoline-2-carboxylic acid tert-butyl ester and 0.270 g (1.5 mol. equiv.) of thianaphthene-2-boronic acid in 4 ml of isopropanol was stirred under argon at room temperature for 30 min. 1 mg (0.45 mol %) of palladium(II)acetate, 4 mg (1.3 mol %) of triphenylphosphine, and 0.6 ml (1.2 mol. equiv.) of 2M sodium bicarbonate aqueous solution were added successively and the mixture was refluxed with stirring for 6 hours. The solvent was evaporated under reduced pressure and the residue was partitioned between 50 ml of ethyl acetate and 25 ml of 5% sodium hydroxide aqueous solution. After shaking, the organic layer was washed with water (25 ml) and brine (25 ml), and then dried with sodium sulfate. The solvent was evaporated under reduced pressure and the remaining oil was crystallized by trituration with n-hexanes. The solid was recrystallized using ethyl acetate\n-hexanes mixture to give 0.41 g (78%) of white solid, mp 137-139° C.

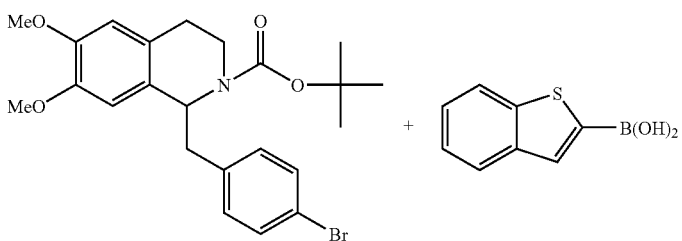

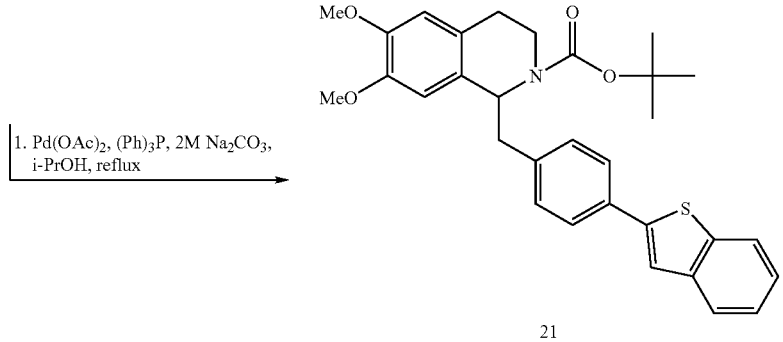

1-(4-Benzo[b]thiophen-2-yl-benzyl)-1,2,3,4-tetrahydro-isoquinoline-6,7-diol hydrobromide (22) was prepared as follows: To a stirred solution of 0.15 g (0.29 mmole) of 1-(4-benzo[b]thiophen-2-yl-benzyl)-6,7-dimethoxy-8-methyl-3,4-dihydro-1-H-isoquinoline-2-carboxylic acid tert-butyl ester in 10 ml of anhydrous dichloromethane under argon at −70° C., 0.9 ml (3 mol. equiv.) of 1M boron tribromide solution in n-hexanes was added. The stirred mixture was allowed to reach room temperature overnight and the solvents were evaporated under reduced pressure. The residue was dissolved in 10 ml of methanol and, again, the solvent was evaporated under reduced pressure. The solid residue was mixed with 10 ml of ether, separated on a glass filter funnel, washed with ether (3×20 ml) to afford an off-white solid, 130 mg (91%), mp 251-254° C.

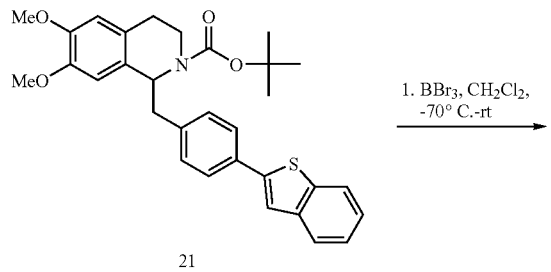

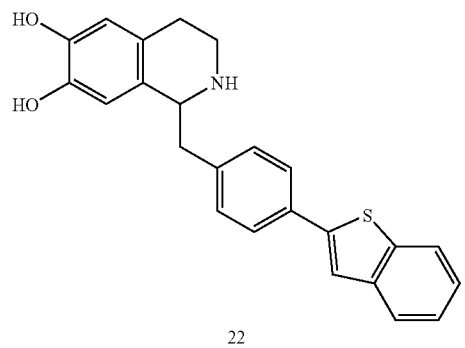

Example 9

Preparation of 6,7-dimethoxy-1-(3'-methoxy-biphenyl-4-ylmethyl)-1,2,3,4-tetrahydro-isoquinoline hydrochloride The intermediate 2-(4-bromo-phenyl)-N-[2-(3,4-dimethoxy-phenyl)-ethyl]-acetamide (31) was prepared as follows: A solution of 4-bromo-phenylacetic acid (10.06 g, 46.8 mmol) and oxalyl chloride (101.9 g, 0.8 mol) in 400 mL of benzene was refluxed for 6 h. The solution was evaporated with benzene 3 times and dried in vacuum. A solution of 4-bromo-phenylacetic acid chloride (1.1 mol. equiv.) in $CH_2Cl_2$ was added to a mixture of 300 mL of 1N NaOH and solution of 3,4-di-methoxy-phenethylamine (6.55 g, 36.1 mmol) in 300 mL of $CH_2Cl_2$. The reaction mixture was stirred overnight at room temperature. Another portion of acid chloride (0.1 eq.) in 20 mL of $CH_2Cl_2$ was added and stirred for 1 h. Organic phase was separated, washed with 1N HCl, 1N NaOH, water, dried over $Na_2SO_4$, filtered and evaporated. A residue was crystallized from EtOAc-hexanes mixture. Yield is 11.54 g (84.5%).

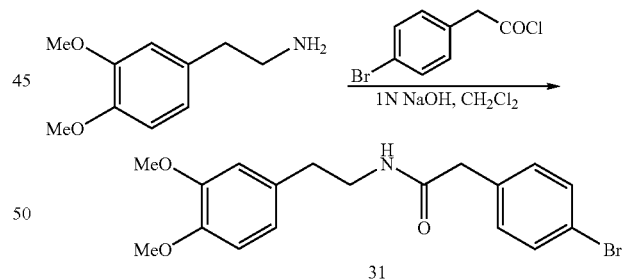

1-(4-bromo-benzyl)-6,7-dimethoxy-1,2,3,4-tetrahydro-isoquinoline oxalate (32) was prepared as follows: A solution of 2-(4-bromo-phenyl)-N-[2-(3,4-dimethoxy-phenyl)-ethyl]-acetamide (1.912 g, 5.05 mmol) and phosphorus oxychloride (24.68 g, 161 mmol) in 50 mL of dry acetonitrile was refluxed for 5 h, cooled, concentrated, evaporated with methanol 3 times and finally dissolved in 50 mL of methanol. Sodium borohydride (3.32 g, 87.8 mmol) was added by small portions. The reaction mixture was stirred overnight at room temperature, concentrated, dissolved in chloroform, washed with 1N NaOH (3 times), dried over $Na_2SO_4$, concentrated and finally dissolved in methanol. A solution of $(COOH)_2 \cdot 2H_2O$ (1.28 g, 10.2 mmol) in MeOH was added. The product was crystallized from MeOH—Et₂O mixture. Yield 1.544 g (66%).

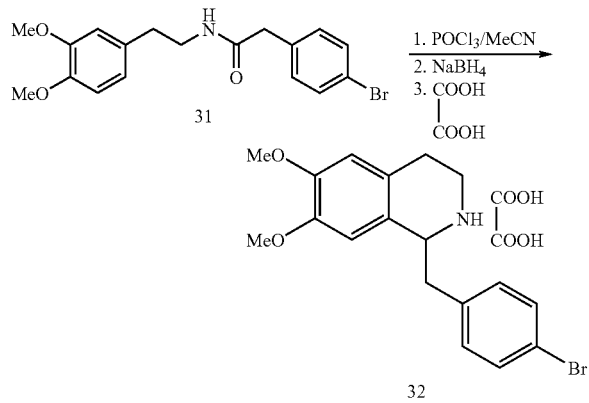

1-(4-bromo-benzyl)-6,7-dimethoxy-1,2,3,4-tetrahydro-isoquinoline hydrochloride (33) was prepared as follows: 1-(4-bromo-benzyl)-6,7-dimethoxy -1,2,3,4-tetrahydro-isoquinoline oxalate (1.24 g, 2.74 mmol) was added to a mixture of 50 mL CH₂Cl₂ and 50 ml of 1N NaOH. The reaction mixture was stirred at room temperature. After dissolving of precipitate, the organic phase was separated, dried over Na₂SO₄, filtered, and evaporated. A residue was dissolved in MeOH and 10 mL of 1M solution of HCl in Et₂O was added. Hydrochloride was crystallized from MeOH—Et₂O mixture. Yield is 0.958 g (87.6%).

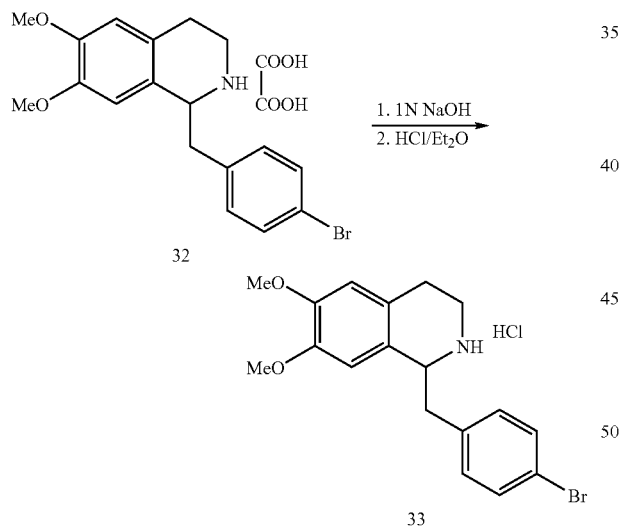

6,7-dimethoxy-1-(3'-methoxy-biphenyl-4-ylmethyl)-1,2,3,4-tetrahydro-isoquinoline hydrochloride (35) was prepared as follows: 1-(4-bromo-benzyl)-6,7-dimethoxy-1,2,3,4-tetrahydro-isoquinoline hydrochloride (0.403 g, 1.01 mmol) was added to a mixture of 20 mL CH₂Cl₂ and 20 ml of 1N NaOH. The reaction mixture was stirred at room temperature. After dissolving of precipitate, the organic phase was separated, dried over Na₂SO₄, filtered, and evaporated. A residue was dissolved in 5 mL i-PrOH and 3-methoxy-phenyl-boronic acid (0.170 g, 1.12 mmol) was added. The resulting solution was stirred for 30 min at room temperature. Pd(OAc)₂ (3 mg, 0.0134 mmol), PPh₃ (8 mg, 0.0305 mmol) and 2N Na₂CO₃ (0.7 mL, 1.4 mmol) were added, the reaction mixture was refluxed for 6 h under Ar and evaporated. A residue was dissolved in chloroform and washed with 1N NaOH. The organic phase was dried under Na₂SO₄, filtered, and evaporated. A residue was dissolved in MeOH, and a solution of oxalic acid dihydrate (0.264 g, 2.08 mmol) was added under reflux. Oxalic acid salt was crystallized from MeOH—Et₂O mixture. Oxalic acid salt was added to a mixture of 20 mL CH₂Cl₂ and 20 ml of 1N NaOH. The reaction mixture was stirred at room temperature. After dissolving of precipitate, the organic phase was separated, dried over Na₂SO₄, filtered, and evaporated. A residue was dissolved in MeOH and 5 mL of 1M solution of HCl in Et₂O was added. Hydrochloride was crystallized from the MeOH—Et₂O mixture. Yield is 0.245 g (56.9%).

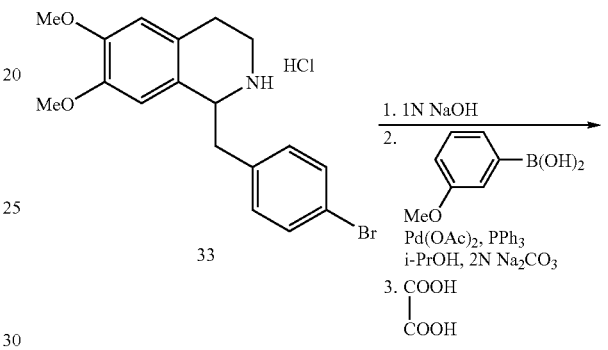

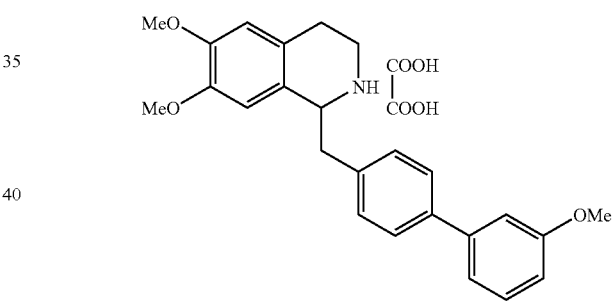

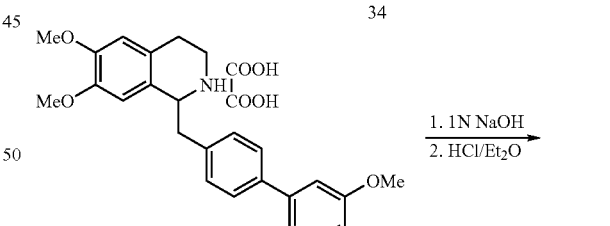

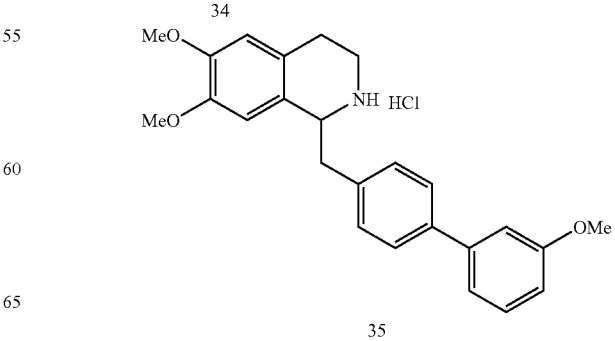

Example 10

Preparation of 6,7-dimethoxy-1-(4'-methyl-biphenyl-4-ylmethyl)-1,2,3,4-tetrahydro-isoquinoline oxalate 6,7-dimethoxy-1-(4'-methyl-biphenyl-4-ylmethyl)-1,2,3,4-tetrahydro-isoquinoline oxalate (36) was prepared as follows: 1-(4-bromo-benzyl)-6,7-dimethoxy-1,2,3,4-tetrahydro-isoquinoline hydrochloride (0.452 g, 1 mmol) was added to a mixture of 20 mL $CH_2Cl_2$ and 20 ml of 1N NaOH. The reaction mixture was stirred at room temperature. After dissolving of precipitate organic phase was separated, dried over $Na_2SO_4$, filtered and evaporated. A residue was dissolved in 6 mL i-PrOH. 4-Methyl-phenyl-boronic acid (0.148 g, 1.09 mmol) was added. The resulting solution was stirred for 30 min at room temperature. $Pd(OAc)_2$ (1 mg, 0.0045 mmol), $PPh_3$ (7 mg, 0.0267 mmol) and 2N $Na_2CO_3$ (1 mL, 2 mmol) were added, the reaction mixture was refluxed for 6 h under Ar and evaporated. A residue was dissolved in chloroform and washed with 1N NaOH. Organic phase was dried under $Na_2SO_4$, filtered and evaporated. A residue was dissolved in MeOH, a solution of oxalic acid dihydrate (0.265 g, 2.1 mmol) was added under reflux. Oxalic acid salt was crystallized from MeOH—$Et_2O$ mixture. Yield is 0.219 g (47.3%).

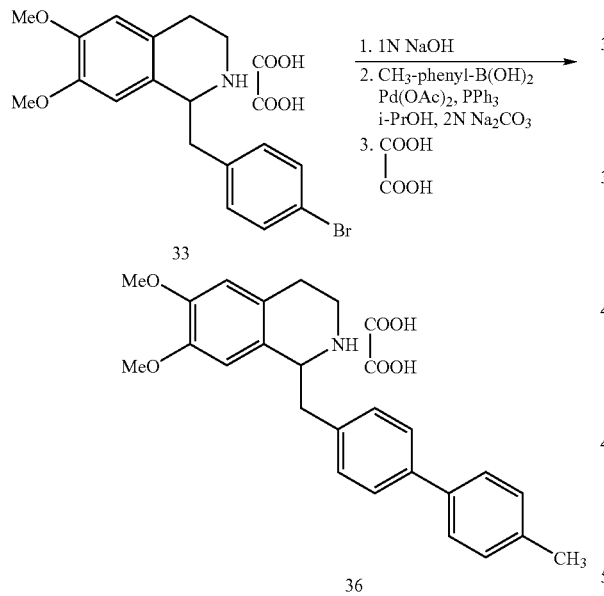

Example 11

Preparation of 1-(4'-Fluoro-biphenyl-4-ylmethyl)-6,7-dimethoxy-1,2,3,4-tetrahydro-isoquinoline oxalate 1-(4'-Fluoro-biphenyl-4-ylmethyl)-6,7-dimethoxy-1,2,3,4-tetrahydro-isoquinoline oxalate (37) was prepared as follows: 1-(4-bromo-benzyl)-6,7-dimethoxy-1,2,3,4-tetrahydro-isoquinoline oxalate (0.452 g, 1 mmol) was added to a mixture of 20 mL $CH_2Cl_2$ and 20 ml of 1N NaOH. The reaction mixture was stirred at room temperature. After dissolving of precipitate organic phase was separated, dried over $Na_2SO_4$, filtered and evaporated. A residue was dissolved in 6 mL i-PrOH. 4-Fluoro-phenyl-boronic acid (0.153 g, 1.09 mmol) was added. The resulting solution was stirred for 30 min at room temperature. $Pd(OAc)_2$ (1 mg, 0.0045 mmol), $PPh_3$ (9 mg, 0.034 mmol) and 2N $Na_2CO_3$ (1 mL, 2 mmol) were added, the reaction mixture was refluxed for 6 h under Ar and evaporated. A residue was dissolved in chloroform and washed with 1N NaOH. Organic phase was dried under $Na_2SO_4$, filtered and evaporated. A residue was dissolved in MeOH, a solution of oxalic acid dihydrate (0.259 g, 2.05 mmol) was added under reflux. Oxalic acid salt was crystallized from MeOH—$Et_2O$ mixture. Yield is 0.294 g (62.9%).

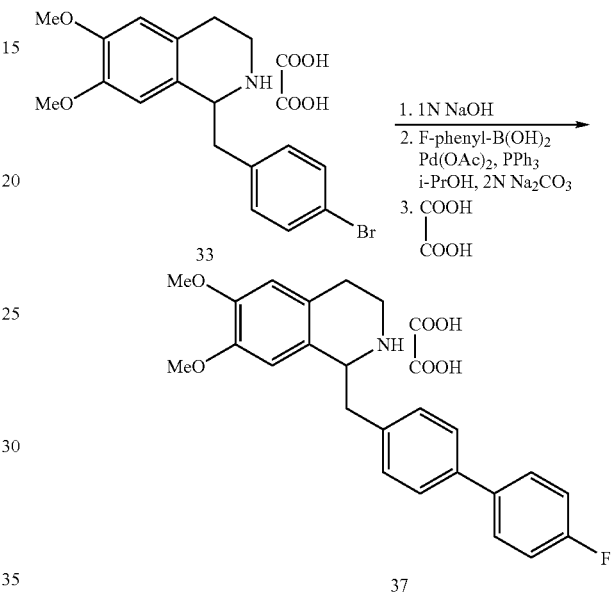

Example 12

Preparation of 1-Biphenyl-3-ylmethyl-6,7-dimethoxy-1,2,3,4-tetrahydro-isoquinoline oxalate 2-(3-Bromo-phenyl)-N-[2-(3,4-dimethoxy-phenyl)-ethyl]-acetamide (41) was prepared as follows: A solution of 3-bromo-phenylacetic acid (2.0 g, 9.3 mmol) and oxalyl chloride (36.4 g, 0.287 mol) in 80 mL of benzene was refluxed for 6 h. The solution was evaporated with benzene 3 times and dried in vacuum. A solution of 3-bromo-phenylacetic acid (1.1 eq.) in $CH_2Cl_2$ was added to mixture of 100 mL of 1N NaOH and solution of 3,4-di-methoxy-phenethylamine (1.31 g, 7.22 mmol) in 100 mL of $CH_2Cl_2$. The reaction mixture was stirred overnight at r.t. Another portion of acid chloride (0.1 eq.) in 10 mL of $CH_2Cl_2$ was added and stirred for 1 h. Organic phase was separated, washed with 1N HCl, 1N NaOH, water, dried over $Na_2SO_4$, filtered and evaporated. A residue was crystallized from EtOAc-hexanes mixtures. Yield is 2.59 g (95%).

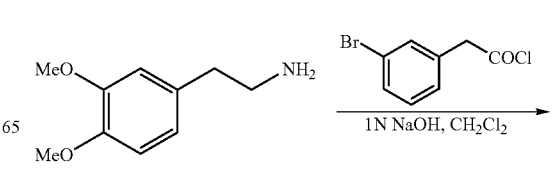

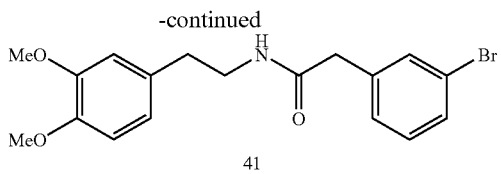

41

1-(3-bromo-benzyl)-6,7-dimethoxy-1,2,3,4-tetrahydro-isoquinoline oxalate (42) was prepared as follows: A solution of 2-(3-bromo-phenyl)-N-[2-(3,4-dimethoxy-phenyl)-ethyl]-acetamide (2.53 g, 6.7 mmol) and phosphorus oxychloride (24.68 g, 161 mmol) in 120 mL of dry acetonitrile was refluxed for 5 h, cooled, concentrated, evaporated with methanol 3 times, and finally dissolved in 50 mL of methanol. Sodium borohydride (3.23 g, 85.4 mmol) was added by small portions. The reaction mixture was stirred overnight at room temperature, concentrated, dissolved in chloroform, washed with 1N NaOH (3 times), dried over $Na_2SO_4$, concentrated, and finally dissolved in methanol. A solution of $(COOH)_2 \cdot 2H_2O$ (1.76 g, 14 mmol) in MeOH was added. The product was crystallized from MeOH—$Et_2O$ mixture. Yield is 1.767 g (58.5%).

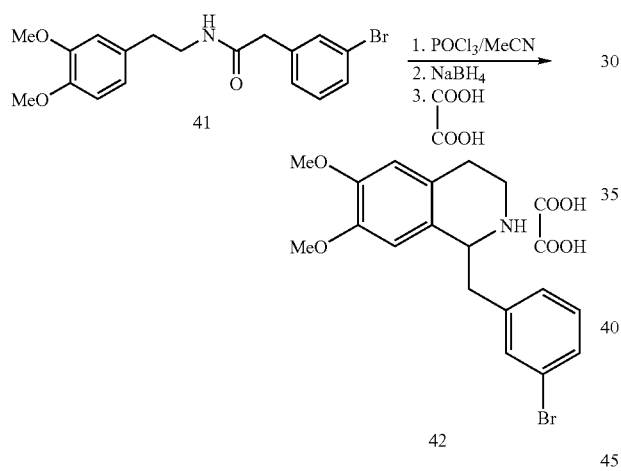

1-biphenyl-3-ylmethyl-6,7-dimethoxy-1,2,3,4-tetrahydro-isoquinoline oxalate (43) was prepared as follows: 1-(3-bromo-benzyl)-6,7-dimethoxy-1,2,3,4-tetrahydro-isoquinoline oxalate (0.910 g, 2.01 mmol) was added to a mixture of 50 mL $CH_2Cl_2$ and 50 ml of 1N NaOH. The reaction mixture was stirred at room temperature. After dissolving of precipitate organic phase was separated, dried over $Na_2SO_4$, filtered and evaporated. A residue was dissolved in 10 mL i-PrOH. Phenyl-boronic acid (0.268 g, 2.2 mmol) was added. The resulting solution was stirred for 30 min at room temperature. $Pd(OAc)_2$ (2 mg, 0.0089 mmol), $PPh_3$ (11 mg, 0.042 mmol) and 2N $Na_2CO_3$ (1.3 mL, 2.6 mmol) were added, the reaction mixture was refluxed for 6 h under Ar and evaporated. A residue was dissolved in chloroform and washed with 1N NaOH. Organic phase was dried under $Na_2SO_4$, filtered and evaporated. A residue was dissolved in MeOH, a solution of oxalic acid dihydrate (0.510 g, 4.05 mmol) was added under reflux. Oxalic acid salt was crystallized from MeOH—$Et_2O$ mixture. Yield is 0.558 g (61.7%)

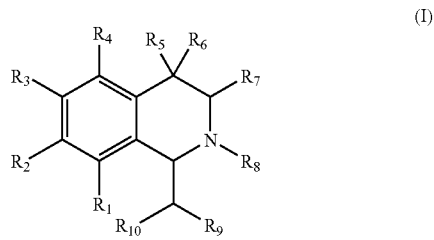

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A compound according to formula (I)

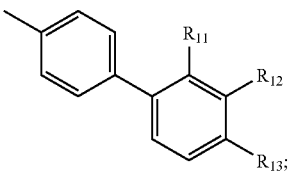

wherein,
$R_1$, $R_2$, $R_3$, and $R_4$ are independently hydrogen or hydroxyl;
$R_5$, $R_6$, $R_7$ are independently hydrogen or alkyl;
$R_8$ is hydrogen, alkyl, aryl, or arylalkyl;
$R_9$ is $R_{10}$ is hydrogen; and $R_{11}$, and $R_{12}$ and $R_{13}$ are independently hydrogen, hydroxyl, halide, alkyl, arylalkyl, alkenyl, arylalkenyl, alkoxy, aryloxy, amino, alkylamino, dialkylamino, arylamino, aryl, or cyclohexyl.

2. A compound as in claim 1 wherein $R_2$ and $R_3$ are hydroxyl and $R_{11}$, $R_{12}$, and $R_{13}$ are hydrogen.

3. The compound according to claim 2 wherein the compound is 6,7-bis-hydroxy-1-biphenyl-4-ylmethyl-1,2,3,4-tetrahydro-isoquinoline or 6,7-bis-methoxy-1-biphenyl-4-ylmethyl-1,2,3,4-tetrahydro-isoquinoline.

4. The compound according to claim 2 wherein the compound is 1-[1,1';4', 1"]terphenyl-4-ylmethyl-1,2,3,4-tetrahydro-isoquinoline-6,7-diol.

5. The compound according to claim 1 wherein the compound is 1-(4'-fluoro-biphenyl-4-ylmethyl)-6,7-dimethoxy-1,2,3,4-tetrahydro-isoquinoline, 1-biphenyl-3-ylmethyl-6,7-dimethoxy-1,2,3,4-tetrahydro-isoquinoline, 6,7-dimethoxy-1-(3'-methoxy-biphenyl-4-ylmethyl)-1,2,3,4-tetrahydroisoquinoline, or 1-(4-benzo[b]thiophen-2-yl-benzyl)-1,2,3,4-tetrahydro-isoquinoline-6,7-diol.

6. A pharmaceutical composition comprising a therapeutically effective amount of at least one compound of claim 1 or a pharmaceutically acceptable salt thereof in combination with at least one pharmaceutically acceptable carrier.

7. A method of preparing a tetrahydroisoquinoline compound according to claim 1 wherein $R_9$ is

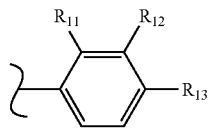

comprising:
reacting a precursor of formula (IA)

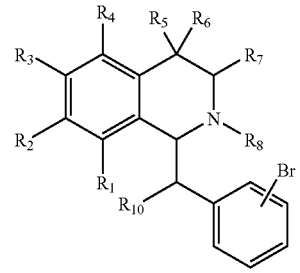

(IA)

with Q—B(OH)$_2$ under conditions effective to replace the bromo group with —Q at the ortho, meta, or para position, wherein Q is alkyl, arylalkyl, alkenyl, arylalkenyl, alkoxy, aryloxy, aryl, cyclohexyl, or

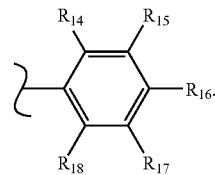

* * * * *